(12) United States Patent
Ishizuka et al.

(10) Patent No.: US 10,858,491 B2
(45) Date of Patent: Dec. 8, 2020

(54) POROUS PARTICLE MADE OF ORGANIC POLYMER, METHOD FOR PRODUCING POROUS PARTICLE MADE OF ORGANIC POLYMER, AND BLOCK COPOLYMER

(71) Applicants: KYOTO UNIVERSITY, Kyoto (JP); EMAUS KYOTO, INC., Kyoto (JP); KOSEN NATIONAL INSTITUTE OF TECHNOLOGY, Hachioji (JP)

(72) Inventors: Norio Ishizuka, Kyoto (JP); Kyoko Konishi, Kyoto (JP); Toshikazu Oda, Kyoto (JP); Yoshinobu Tsujii, Kyoto (JP); Keita Sakakibara, Kyoto (JP); Takaya Sato, Yamagata (JP)

(73) Assignees: Kyoto University, Kyoto (JP); Emaus Kyoto, Inc., Kyoto (JP); Kosen National Institute of Technology, Tokyo (JP)

( * ) Notice: Subject to any disclaimer, the term of this patent is extended or adjusted under 35 U.S.C. 154(b) by 58 days.

(21) Appl. No.: 15/751,743

(22) PCT Filed: Aug. 5, 2016

(86) PCT No.: PCT/JP2016/073211
§ 371 (c)(1),
(2) Date: Feb. 9, 2018

(87) PCT Pub. No.: WO2017/026426
PCT Pub. Date: Feb. 16, 2017

(65) Prior Publication Data
US 2018/0230284 A1 Aug. 16, 2018

(30) Foreign Application Priority Data
Aug. 10, 2015 (JP) .................... 2015-158587

(51) Int. Cl.
*C08J 9/28* (2006.01)
*C08G 59/32* (2006.01)
(Continued)

(52) U.S. Cl.
CPC ............ *C08J 9/286* (2013.01); *A61K 8/81* (2013.01); *A61K 8/84* (2013.01); *B01J 20/264* (2013.01);
(Continued)

(58) Field of Classification Search
CPC ............... B01J 20/28016; B01J 20/203064
See application file for complete search history.

(56) References Cited

U.S. PATENT DOCUMENTS

| | | |
|---|---|---|
| 2006/0204527 A1 | 9/2006 | Miyamoto |
| 2007/0128424 A1 | 6/2007 | Omori et al. |

(Continued)

FOREIGN PATENT DOCUMENTS

| | | |
|---|---|---|
| EP | 2 139 942 | 1/2010 |
| JP | 58-104017 | 6/1983 |

(Continued)

OTHER PUBLICATIONS

Machine translation WO 2013/161098 (Year: 2013).*

(Continued)

*Primary Examiner* — Alexandre F Ferre
(74) *Attorney, Agent, or Firm* — Hamre, Schumann, Mueller & Larson, P.C.

(57) ABSTRACT

The present invention provides porous particles made of an organic polymer, uniform in shape, and having through holes that are not closed. The porous particles according to the present invention are porous particles having a substantially spherical shape. The porous particles are made of an organic polymer. Each of the porous particles has an interconnected pore structure in which through holes provided (Continued)

Example 1
Photograph of appearance of particles (250 × magnification)

inside the porous particle communicate with each other, and ends of the through holes are open toward an outside of the porous particle.

9 Claims, 6 Drawing Sheets

(51) Int. Cl.
  C08G 59/50 (2006.01)
  C08F 22/10 (2006.01)
  C08F 293/00 (2006.01)
  A61K 8/81 (2006.01)
  A61K 8/84 (2006.01)
  B01J 20/28 (2006.01)
  C08J 9/00 (2006.01)
  B01J 20/26 (2006.01)
  B01J 20/285 (2006.01)
  B01J 20/30 (2006.01)

(52) U.S. Cl.
  CPC ....... *B01J 20/285* (2013.01); *B01J 20/28016* (2013.01); *B01J 20/3064* (2013.01); *C08F 22/1006* (2020.02); *C08F 293/00* (2013.01); *C08F 293/005* (2013.01); *C08G 59/3218* (2013.01); *C08G 59/3245* (2013.01); *C08G 59/5026* (2013.01); *C08J 9/0061* (2013.01); *C08J 2201/0543* (2013.01); *C08J 2205/05* (2013.01); *C08J 2335/02* (2013.01); *C08J 2363/00* (2013.01); *C08J 2453/00* (2013.01)

(56) References Cited

U.S. PATENT DOCUMENTS

| | | | |
|---|---|---|---|
| 2009/0285894 A1* | 11/2009 | Wang | C08J 9/28 424/486 |
| 2010/0264084 A1 | 10/2010 | Midorikawa et al. | |
| 2011/0212179 A1 | 9/2011 | Liu | |
| 2011/0223529 A1 | 9/2011 | Shimanaka et al. | |
| 2013/0052117 A1 | 2/2013 | Imai et al. | |
| 2013/0184145 A1 | 7/2013 | Takahashi et al. | |
| 2013/0196064 A1 | 8/2013 | Shimanaka et al. | |
| 2014/0101930 A1 | 4/2014 | Ito et al. | |
| 2015/0182943 A1* | 7/2015 | Shibata | B01D 15/40 502/402 |
| 2016/0089334 A1 | 3/2016 | Nakayama et al. | |

FOREIGN PATENT DOCUMENTS

| | | |
|---|---|---|
| JP | 11-092568 | 4/1999 |
| JP | 2003-342409 | 12/2003 |
| JP | 2004-143026 | 5/2004 |
| JP | 2004-262962 | 9/2004 |
| JP | 2005-112847 | 4/2005 |
| JP | 2005-162504 | 6/2005 |
| JP | 2006-104016 | 4/2006 |
| JP | 2006-346546 | 12/2006 |
| JP | 2012-092318 | 5/2012 |
| JP | 2013-020960 | 1/2013 |
| JP | 2014-148456 | 8/2014 |
| JP | 2015-003860 | 1/2015 |
| JP | 2015-083688 | 4/2015 |
| JP | 5733608 B | 6/2015 |
| WO | 2005/056175 | 6/2005 |
| WO | 2010/013651 | 2/2010 |
| WO | 2010/062678 | 6/2010 |
| WO | 2013/161098 | 10/2013 |
| WO | 2014/186328 | 11/2014 |
| WO | 2014/188924 | 11/2014 |

OTHER PUBLICATIONS

Partial European Search Report for the related/corresponding European Patent Application No. 16835123.7 dated Dec. 10, 2018, 13 pages.
Gokmen et al., "Porous polymer particles—A comprehensive guide to synthesis, characterization, functionalization and applications", Progress in Polymer Science, vol. 37, No. 3, pp. 365-405 (2012).
Office Action for the related Japanese Patent Application No. 2017-534430 dated Jan. 15, 2019, 8 pages with a partial translation.
Partial European Search Report for the corresponding/related European Patent Application No. 16835121.1 dated Feb. 19, 2019, 14 pages.
Office Action issued in related Japanese Patent Application Serial No. 2017-534430, dated Aug. 13, 2019, 5 pages with an English translation.

* cited by examiner

Example 1
Photograph of appearance of particles (250× magnification)

Example 1
Photograph of appearance of particles (1000× magnification)

Example 1
Photograph of surface of particles (5000× magnification)

Example 1
Internal cross section of particle (10000 × magnification)

Example 7
Photograph of appearance of particles (1000× magnification)

Example 7
Internal cross section of particle (50000× magnification)

POROUS PARTICLE MADE OF ORGANIC POLYMER, METHOD FOR PRODUCING POROUS PARTICLE MADE OF ORGANIC POLYMER, AND BLOCK COPOLYMER

TECHNICAL FIELD

The present invention relates to porous particles made of an organic polymer, a method for producing porous particles made of an organic polymer, and a block copolymer.

BACKGROUND ART

Porous materials having an interconnected pore structure in which through holes communicate with each other are used for various purposes. Examples of such porous materials include those made of organic polymers (Patent Document 1 etc.) and those made of silica gel (Patent Documents 2 to 3 etc.). In recent years, porous materials in the form of particles have been proposed. Such porous particles can be produced by, for example, producing a porous material in the form of a single mass and then processing it into particles by pulverization (Patent Document 2) or producing porous particles in the first place (Patent Document 3).

CITATION LIST

Patent Document(s)

Patent Document 1: JP-A-2013-020960
Patent Document 2: JP-A-2014-148456
Patent Document 3: JP-A-2015-3860

BRIEF SUMMARY OF THE INVENTION

Problem to be Solved by the Invention

A porous material having an interconnected pore structure in which through holes communicate with each other is advantageous in that, for example, it can be handled more easily than a porous material in the form of a single mass when used as a filler or a column reactor in a separation column for chromatography. However, the method in which a porous material in the form of a single mass is produced and then processed into particles by pulverization has a problem in that the thus-produced porous particles have indefinite shapes, so that they may achieve low filler loading. On the other hand, with the method in which the porous material in the form of particles is produced in the first place, through holes may be closed by skin layers formed on surfaces of the particles.

With the foregoing in mind, it is an object of the present invention to provide porous particles made of an organic polymer, uniform in shape, and having through holes that are not closed, a method for producing the porous particles, and a block copolymer for use in the production method.

Means for Solving Problem

In order to achieve the above object, the present invention provides porous particles having a substantially spherical shape, wherein the porous particles are made of an organic polymer, each of the porous particles has an interconnected pore structure in which through holes provided inside the porous particle communicate with each other, and ends of the through holes are open toward an outside of the porous particle.

The present invention also provides a method for producing the porous particles according to the present invention, including: a dispersion preparation step of preparing a dispersion by dispersing a porous particle raw material containing an organic monomer and/or an organic prepolymer in a dispersion medium; and a polymerization step of polymerizing the porous particle raw material in the dispersion, wherein, in the polymerization step, the through holes are formed by spinodal decomposition.

The present invention also provides a block copolymer including: a hydrophobic polymer block; and a hydrophilic polymer block. The block copolymer is used as a dispersant for dispersing the porous particle raw material in the dispersion medium in the dispersion preparation step of the porous particle production method according to the present invention.

Effects of the Invention

The porous particles of the present invention are configured so that: the porous particles are made of an organic polymer and substantially spherical and uniform in shape, through holes are provided inside each particle, and the through holes are not closed. Further, according to the porous particle production method of the present invention and the block copolymer of the present invention, it is possible to produce the porous particles of the present invention with the above-described configuration.

MODE FOR CARRYING OUT THE INVENTION

Figure 1:
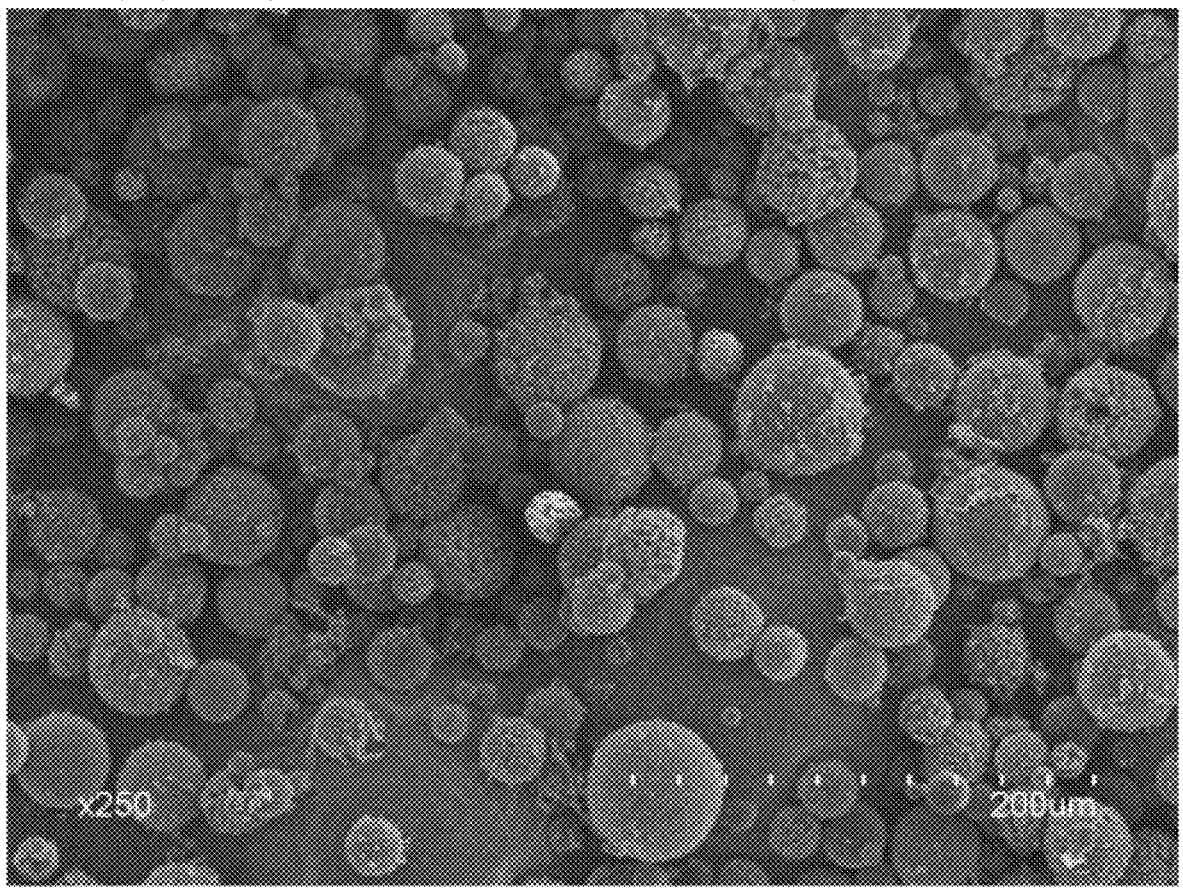
FIG. 1 is a photograph showing the appearance of epoxy resin porous particles produced in an example (250× magnification).

The present invention will be described below with reference to illustrative examples. It is to be noted, however, that the present invention is by no means limited by the following descriptions.

[1. Porous Particles Made of Organic Polymer]

As described above, the porous particles made of an organic polymer according to the present invention (may be referred to simply as "porous particles" or "porous particles of the present invention" hereinafter) are substantially spherical. Each porous particle of the present invention is shaped so that, for example, the longest diameter (the diameter with a maximum length) is, for example, not more than 1.6 times, not more than 1.4 times, or not more than 1.2 times the shortest diameter (the diameter with a minimum length). Ideally, the porous particle of the present invention is completely spherical with the longest diameter being the same as the shortest diameter, for example.

The particle size (particle diameter) of the porous particles of the present invention is not particularly limited, and may be such that the lower limit of the mean particle size is, for example, 0.5 µm, 5 µm, 7 µm, or 1,000 µm (1 mm), and the upper limit of the mean particle size is, for example, 30,000 µm (30 mm), 10,000 µm (10 mm), 1,000 µm (1 mm), or 700 µm. The particle size (particle diameter) of the porous particles of the present invention is in the range from, for example, 0.5 to 30,000 µm (0.5 µm to 30 mm), 1 to 10 mm, 5 to 1,000 µm, or 7 to 700 µm. In the present invention, the mean particle size can be measured by a laser diffraction/light scattering particle size distribution analyzer, for example. Alternatively, in the case where the measurement by a laser diffraction/light scattering particle size distribution analyzer is difficult owing to an insufficient amount of a sample, the mean particle size may be estimated roughly from a scanning electron microscope photograph (SEM) image(s).

As described above, the porous particles of the present invention are made of an organic polymer, each of the porous particles has an interconnected pore structure in which through holes provided inside the porous particle communicate with each other, and ends of the through holes are open toward the outside of the porous particle. Owing to the interconnected pore structure, the through holes are bent, for example. The porous particles of the present invention have through holes with a co-continuous structure (an interconnected pore structure in which the through holes provided inside the porous particle communicate with each other), instead of a particle agglutination type structure pore structure. In the present invention, the term "particle agglutination type" pore structure refers to a structure in which small particles without holes inside are bound to each other to form a skeleton and also to form pores as hollow spaces among the particles at the same time. When a collection of the particles having the above-described "particle agglutination type" pore structure form a substantially particulate outer shape, it is referred to as a particle agglutination type particle.

Whether the porous particle of the present invention has an interconnected pore structure in which through holes communicate with each other can be checked by, for example, examining a photograph showing the cross section or the surface of the porous particle of the present invention. Whether ends of the through holes are open toward the outside of the porous particle can be checked by, for example, examining a photograph showing the surface of the porous particle of the present invention. The porous particle of the present invention does not have a skin layer (a layer coating the surface of the particle), for example, so that the ends of the through holes are open toward the outside of the porous particle without being closed. The presence or absence of the skin layer also can be checked by examining a photograph showing the surface of the porous particle of the present invention. It is preferable that the porous particles are separate from each other without being bound to each other.

The porous particles of the present invention may each be a collection of a plurality of porous particles that are separate from each other without being bound to each other. In the collection of the porous particles, the number of substantially spherical porous particles (the porous particles of the present invention) is over 50%, for example, and may be 70% or more, 80% or more, 90% or more, or the like.

In the porous particles of the present invention, the interconnected pore structure in which the through holes communicate with each other may be, for example, an open-cell structure in which walls between interconnected macropores have mesopores. The diameter of the through hole is not particularly limited, and is, for example, in the range from 10 to 1,000,000 nm (1 mm), 20 to 100,000 nm, or 30 to 50,000 nm. The diameter of the through hole also may be referred to as "pore diameter" hereinafter. As will be described below, the pore diameter is influenced by various factors during the production of the porous particles of the present invention. Thus, the pore diameter can be adjusted by adjusting the various factors. The pore diameters of the respective through holes generally are not uniform, and the degree of uniformity (dispersion) varies depending on the influence of, for example, heat distribution in a polymerization reaction system and stirring operations during the production of the porous particles of the present invention.

The porosity (void fraction) of the porous particle of the present invention is not particularly limited, and is, for example, 30 to 95 vol %, 35 to 90 vol %, or 40 to 85 vol %. The porosity (void fraction) can be measured by nitrogen adsorption, mercury intrusion, or liquid chromatography, for example.

The material of the porous particles of the present invention is not particularly limited as long as it is an organic polymer. The organic polymer is not particularly limited and may be any organic polymer. Examples of the organic polymer include epoxy resins, polyethylene derivatives, poly(meth)acrylic acids, and poly(meth)acrylic acid derivatives. The polyethylene derivatives may be, for example, derivatives having any substituent in the side chains, and specific examples thereof include polymers such as styrene, vinyltoluene, and divinylbenzene. The poly(meth)acrylic acid derivatives may be, for example, any poly(meth)acrylic esters. Specific examples of the poly(meth)acrylic esters include: alkyl esters of poly(meth)acrylic acids, such as methyl poly(meth)acrylate, ethyl poly(meth) acrylate, and lauryl poly(meth) ethyl; and (poly)ethylene glycol esters of poly(meth)acrylic acids. In the present invention, the term "(meth)acrylic" means either or both of "acrylic" and "methacrylic", and the term "(co)polymerize (and grammatical variations thereof)" means either or both of "polymerize" and "copolymerize". The same applies to the term "(meth) acrylate". The term "(poly)alkylene . . . " means either or both of "alkylene . . . " and "polyalkylene . . . ". The same applies to the term "(poly)ethylene . . . ".

Examples of the epoxy resins include aromatic epoxy resins, aliphatic epoxy resins, alicyclic epoxy resins, and heterocyclic epoxy resins. More specific examples of the epoxy resins include bisphenol A-type epoxy resins, bisphenol F-type epoxy resins, bisphenol AD-type epoxy resins, fluorine-containing epoxy resins, triglycidyl isocyanurate, alicyclic glycidyl ether-type epoxy resins, alicyclic glycidyl ester-type epoxy resins, and novolac-type epoxy resins.

The organic polymer may or may not contain a heteroatom such as a nitrogen atom or a sulfur atom in the main chain, for example. The organic polymer may or may not contain a side chain (substituent), and may or may not contain a heteroatom such as a nitrogen atom or a sulfur atom in the side chain, for example.

The porous particles of the present invention may be made of one type of polymer, or may be made of a mixture or copolymer of two or more types of polymers, for example. The copolymer may be a random copolymer or a block copolymer, for example.

The raw material monomer constituting the polymer forming the porous particles of the present invention may be radical polymerizable or ion polymerizable, for example (The same applies to a raw material prepolymer. The same applies hereinafter in this paragraph.). When a radical polymerizable monomer is subjected to free radical polymerization, a polymer of the above-described particle agglutination type is liable to be formed. Thus, in order to cause spinodal decomposition in the present invention, it is preferable to use living radical polymerization that proceeds in a consecutive manner. Ion polymerization and condensation polymerization also are consecutive reactions, so that it can be said they also are suitable for causing spinodal decomposition. The ion polymerizable monomer may be an anion polymerizable monomer or a cation polymerizable monomer, for example. Examples of the radical polymerizable monomer include the above-described polyethylene derivatives and poly(meth)acrylic acid derivatives. Examples of the ion polymerizable monomer include: epoxy monomers; styrene; 1,3 butadiene and derivatives thereof, vinylpyridine, methacrylic esters; and acrylonitrile. The monomer used for forming the porous particle of the present invention may be, for example, a monomer other than the radical polymerizable monomer, and may be an ion polymerizable monomer, for example.

The porous particles of the present invention may or may not contain a component(s) other than the organic polymer. The other component(s) is not particularly limited, and examples thereof include: inorganic fillers (such as silica, calcium carbonate, talc, alumina, titanium oxide, and carbon black); organic fillers (such as acrylic resin particles and urethane resin particles); and nanofibers (such as carbon nanofibers and cellulose nanofibers).

The method for producing the porous particles according to the present invention is not particularly limited. For example, they can be produced by the porous particle production method according to the present invention.

[2. Porous Particle Production Method]

The porous particle production method according to the present invention is, as described above, a method for producing the porous particles according to the present invention, including: a dispersion preparation step of preparing a dispersion by dispersing a porous particle raw material containing an organic monomer and/or an organic prepolymer in a dispersion medium; and a polymerization step of polymerizing the porous particle raw material in the dispersion, wherein, in the polymerization step, the through holes are formed by spinodal decomposition.

In the porous particle production method according to the present invention, for example, in the dispersion preparation step, the porous particle raw material is dispersed in the dispersion medium together with the dispersant. The dispersant may be a surfactant, for example.

In the porous particle production method according to the present invention, the dispersant may be, for example, the block copolymer according to the present invention, containing a hydrophobic polymer block and a hydrophilic polymer block. In this case, for example, the porous particle production method according to the present invention may further include a dispersant production step of producing the dispersant (the block copolymer of the present invention). The dispersant production step may include a first living radical polymerization step of forming one of the hydrophobic polymer block and the hydrophilic polymer block by living radical polymerization and a second living radical polymerization step of forming the other one of the hydrophobic polymer block and the hydrophilic polymer block by living radical polymerization after the first living radical polymerization step. Since the block copolymer of the present invention contains a hydrophobic polymer block and a hydrophilic polymer block, it can be referred to as a "surfactant" in a broad sense.

According to the production method of the present invention, it is possible to produce porous particles having an interconnected pore structure in which through holes communicate with each other, having a substantially spherical outer shape, and having no skin layer. Although the mechanism thereof is unknown, for example, it is speculated that such porous particles can be produced because the interface between the porous particle raw material and the dispersion medium can be maintained in a suitable state. More specifically, it is speculated that, for example, when the interface is maintained in a suitable state, the porous particle raw material can be polymerized without causing agglutination, so that the above-described through holes can be formed. It is also speculated that, since the state where the porous particle raw material is dispersed in the dispersion medium in the form of particles can be maintained, it is possible to produce the substantially spherical porous particles of the present invention, for example. If either one of the hydrophilic substance and the hydrophobic substance contained in the porous particle raw material is present disproportionately at the interface, for example, a skin layer may be formed by polymerization or the like of the substance. The through holes on the surface of the porous particle are likely to be closed by this skin layer. However, by controlling the hydrophilic substance and the hydrophobic substance so as to be present at a suitable ratio at the interface, it is possible to prevent the formation of the skin layer. It is to be noted, however, that this mechanism is merely illustrative and does not limit the present invention by any means.

The method for maintaining the interface between the porous particle raw material and the dispersion medium in a suitable state is not particularly limited, and may be, for example, the use of the surfactant or the block copolymer (dispersant) of the present invention, which is a surfactant in a broad sense. In the surfactant or the block copolymer (dispersant) of the present invention, it is preferable to control the ratio between a hydrophobic moiety and a hydrophilic moiety part appropriately, as will be described below. Another example of the method for maintaining the interface between the porous particle raw material and the dispersion medium in a suitable state is to physically stir the dispersion.

The term "spinodal decomposition" as used in the present invention refers to a phenomenon in which a multi-component mixed system causes phase separation (e.g., a two-component mixed system is separated into two phases) while forming a co-continuous structure, or the state where such phase separation has occurred. The term "spinodal decomposition" generally may be used to refer to the process of two-phase separation caused when a two-component mixed system at a high temperature is brought into an unstable state by quenching the system, for example. However, in the present invention, the term "spinodal decomposition" is not limited to the one caused by quenching. That is, in the present invention, the method for causing the spinodal decomposition is not particularly limited, and may be any method. For example, it is considered that, by dispersing a porous particle raw material in a dispersion medium and polymerizing or crosslinking the porous particle raw material while maintaining the interface between the porous particle raw material and the dispersion medium in a suitable state, the spinodal decomposition is caused and the structure is fixed. The method for maintaining the interface between the porous particle raw material and the dispersion medium in a suitable state is as described above, for example.

The porous particle production method according to the present invention will be described more specifically below.

[2-1. Dispersion]

In the production method of the present invention, first, a dispersion is prepared by dispersing a porous particle raw material containing an organic monomer and/or an organic prepolymer in a dispersion medium (the dispersion preparation step). The organic monomer and the organic prepolymer are not particularly limited, and examples thereof include monomers and prepolymers corresponding to the above-described organic polymers, inorganic polymers, and organic-inorganic hybrid polymers. For example, as the raw material of an epoxy resin, an epoxy monomer and/or an epoxy prepolymer corresponding to each of the above-described epoxy resins can be used, for example. Only one type of epoxy monomer and epoxy prepolymer may be used, or two or more types of them may be used in combination. Examples of the epoxy monomer and the epoxy prepolymer include "TETRAD-C (trade name)" manufactured by Mitsubishi Gas Chemical Company, Inc., "TEPIC (trade name)" manufactured by Nissan Chemical Industries, Ltd., and "EPIKOTE 828 (trade name)" manufactured by Mitsubishi Chemical Corporation.

The epoxy monomer and the epoxy prepolymer may be a polyfunctional-epoxy group-containing compound, for example. The epoxy resin may be obtained by polymerizing the epoxy monomer and the epoxy prepolymer with a curing agent, for example. The curing agent may be a polyfunctional-amino group-containing compound, for example. That is, the epoxy resin may be a polymer of a polyfunctional-epoxy group-containing compound and a polyfunctional-amino group-containing compound, for example. Only one type of epoxy monomer and epoxy prepolymer may be used, or two or more types of them may be used in combination. Only one type of curing agent may be used, or two or more types of curing agents may be used in combination.

The polyfunctional-epoxy group-containing compound is an epoxy compound having two or more epoxy groups in one molecule, preferably having three or more epoxy groups, e.g., three or four epoxy groups, in one molecule. By using a polyfunctional-epoxy group-containing compound having three or more epoxy groups in one molecule, for example, it is possible to produce porous epoxy resin particles having a suitable pore diameter and a suitable strength. The polyfunctional-epoxy group-containing compound may be either an aromatic epoxy compound or a non-aromatic epoxy compound, for example. Also, the polyfunctional-epoxy group-containing compound may be either a high molecular weight compound (e.g., an oligomer or a prepolymer) or a low molecular weight compound (e.g., a monomer), for example.

The aromatic epoxy compound may be, for example, a bisphenol A-type epoxy compound, a brominated bisphenol A-type epoxy compound, a bisphenol F-type epoxy compound, a bisphenol AD-type epoxy compound, a stilbene-type epoxy compound, a biphenyl-type epoxy compound, a bisphenol A novolac-type epoxy compound, a cresol novolac-type epoxy compound, diaminodiphenylmethane-type epoxy compound, a polyphenyl-based epoxy compound such as a tetrakis (hydroxyphenyl) ethane-based epoxy compound, a fluorine-containing epoxy compound, or a heteroaromatic ring-containing epoxy compound such as a triazine ring-containing epoxy compound.

The aromatic epoxy compound may be, for example, a bisphenol A-type epoxy compound, a brominated bisphenol A-type epoxy compound, a bisphenol F-type epoxy compound, a bisphenol AD-type epoxy compound, a fluorene-containing epoxy compound, or triglycidyl isocyanurate. Particularly preferably, the aromatic epoxy compound may be a bisphenol A-type epoxy compound, a brominated bisphenol A-type epoxy compound, a bisphenol F-type epoxy compound, a bisphenol AD-type epoxy compound, or a fluorene-containing epoxy compound, each having an epoxy equivalent of 500 or less and a melting point of 100° C. or lower. The aromatic epoxy compound may be N,N,N',N'-tetraglycidyl-m-xylylenediamine (the compound obtained by replacing the cyclohexane ring in the chemical formula (1) shown below by a benzene ring), for example.

The non-aromatic epoxy compound is, for example, an aliphatic glycidyl ether-type epoxy compound, an aliphatic glycidyl ester-type epoxy compound, an alicyclic glycidyl ether-type epoxy compound, or an alicyclic glycidyl ester-type epoxy compound. Preferably, the non-aromatic epoxy compound is an alicyclic glycidyl ether-type epoxy compound, an alicyclic glycidyl ester-type epoxy compound, or the like. Particularly preferably, the non-aromatic epoxy compound is an alicyclic glycidyl ether-type epoxy compound or an alicyclic glycidyl ester-type epoxy compound each having an epoxy equivalent of 500 or less and a melting point of 100° C. or below.

The non-aromatic epoxy compound preferably is an alicyclic epoxy compound having three or more epoxy groups, e.g., three or four epoxy groups, in one molecule, for the reason described above.

The alicyclic epoxy compound having three or more epoxy groups in one molecule is not particularly limited, and an alicyclic epoxy compound having an alicyclic hydrocarbon group and three or more epoxy groups can be used as appropriate. From the viewpoint of further enhancing the hydrophilicity, it is preferable that the alicyclic epoxy compound contains nitrogen atoms. The alicyclic epoxy compound containing nitrogen atoms may be a compound represented by the following chemical formula (A), for example.

$$X\text{-}(NY_2)_m \qquad (A)$$

In the chemical formula (A), X is an alicyclic hydrocarbon group having 3 to 8 carbon atoms and bound to the nitrogen atom in the formula either directly or via a straight-chain alkylene group having 1 to 5 carbon atoms. Ys may be the same or different from each other, and may each be a hydrogen atom, or an epoxy group bound to the nitrogen atom in the formula either directly or via a straight-chain alkylene group having 1 to 5 carbon atoms. m is 2, 3 or 4 (particularly preferably 2). Y and m are selected in such a manner that three or more epoxy groups are present in the chemical formula (A). The respective "$NY_2$"s may be the same or different from each other.

As described above, X in the chemical formula (A) is an alicyclic hydrocarbon group having 3 to 8 carbon atoms (more preferably 4 to 7, still more preferably 5 to 6) and bound to the nitrogen atom in the formula either directly or via a straight-chain alkylene group having 1 to 5 carbon atoms (more preferably 1 to 3, still more preferably 1). The straight-chain alkylene group that may be present between the nitrogen atom and the alicyclic hydrocarbon group is a methylene group, an ethylene group, a propylene group, or the like, for example. From the viewpoint of preventing deterioration of the mechanical strength of the porous particles, it is preferable that the number of carbon atoms in the straight-chain alkylene group does not exceed the above upper limit. Examples of such an X include groups represented by the following formulae (I) to (VI).

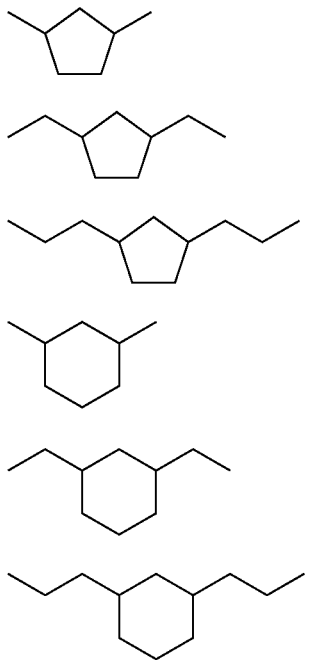

As described above, Y in the chemical formula (A) may be an epoxy group bound to the nitrogen atom in the formula either directly or via a straight-chain alkylene group having 1 to 5 carbon atoms (more preferably 1 to 3, still more preferably 1). The straight-chain alkylene group is not particularly limited, and may be the same as the straight-chain alkylene group described above in connection with X, for example.

As described above, m in the chemical formula (A) is 2, 3, or 4. From the viewpoint of preventing a cross-linking reaction from being inadequate, it is preferable that m is 2 or more. From the viewpoint of preventing a decrease in reactivity caused by steric hindrance, it is preferable that m is 4 or less. As described above, in the respective "NY$_2$"s in the chemical formula (A), Ys may be the same or different from each other, and may each be a hydrogen atom, or an epoxy group bound to the nitrogen atom in the formula either directly or via a straight-chain alkylene group having 1 to 5 carbon atoms. In the respective "NY$_2$"s, it is preferable that at least one Y (preferably, both the two Ys) is the epoxy group. The number of epoxy groups in the chemical formula (A) preferably is not too small from the viewpoint of preventing a cross-linking reaction from being inadequate, and preferably is not too large from the viewpoint of preventing a decrease in reactivity caused by steric hindrance.

Specific examples of the alicyclic epoxy compound having three or more epoxy groups in one molecule include compounds represented by the following chemical formulae (1A) and (1).

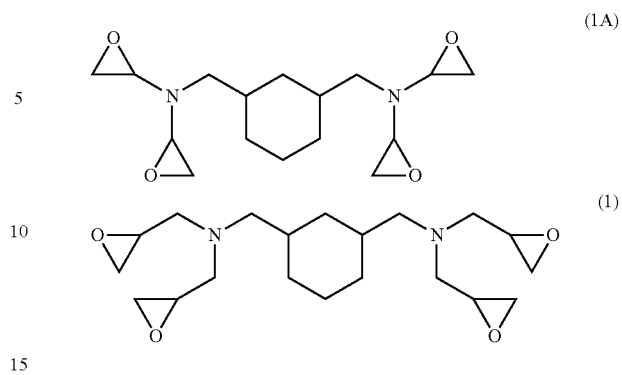

The non-aromatic epoxy compound may be, for example, a compound having an isocyanuric ring, such as "isocyanuric acid triglycidyl", i.e., triglycidyl isocyanurate (2,2,2,-tri-(2,3-epoxypropyl)-isocyanurate), represented by the chemical formula (4) in an example of the present invention to be described below.

From the viewpoint of imparting high hydrophilicity to porous epoxy resin particles to be obtained, the polyfunctional-epoxy group-containing compound preferably has nitrogen atoms. In particular, from the viewpoint of compatibility and reactivity with polyfunctional-amino group-containing compounds and the strength of porous epoxy resin particles to be obtained, N,N,N',N'-tetraglycidyl-m-xylylenediamine is preferable. Also, from the viewpoint of high hydrophilicity and broad utility of the raw material, triglycidyl isocyanurate is preferable.

Only one type of polyfunctional-epoxy group-containing compound may be used, or two or more types of polyfunctional-epoxy group-containing compounds may be used in combination.

The polyfunctional-epoxy group-containing compound used as the raw material of the porous epoxy resin particles may be either an aromatic amino compound or a non-aromatic amino compound, for example.

Examples of the aromatic amino compound include: aromatic amino compounds such as meta-phenylenediamine, diaminodiphenylmethane, diaminodiphenylsulfone, benzyldimethylamine, and dimethylaminomethylbenzene; aromatic acid anhydrides such as phthalic anhydride, trimellitic anhydride, and pyromellitic anhydride; and amino compounds with a heteroaromatic ring(s) like a triazine ring, such as phenol resins and phenol novolac resins. The aromatic amino compound preferably is an aromatic amino compound having two or more primary amino groups in a molecule, particularly preferably meta-phenylenediamine, diaminodiphenylmethane, or diaminodiphenylsulfone.

Examples of the non-aromatic amino compound include: aliphatic amino compounds such as ethylenediamine, diethylenetriamine, triethylenetetramine, tetraethylenepentamine, iminobispropylamine, bis(hexamethylene)triamine, 1,3,6-trisaminomethylhexane, polymethylenediamine, trimethylhexamethylenediamine, and polyether diamine; alicyclic amino compounds such as isophorone diamine, menthane diamine, N-aminoethylpiperazine, 3,9-bis(3-aminopropyl)2,4,8,10-tetraoxaspiro(5,5)undecane adduct, bis(4-amino-3-methylcyclohexyl)methane, bis(4-aminocyclohexyl)methane, and modifications thereof; and aliphatic polyamide amino compounds each composed of a polyamino compound and a dimer acid.

Among them, from the viewpoint of achieving a cross-linking reaction efficiently, alicyclic amino compounds having two or more primary amino groups in a molecule are preferable. It is more preferable that the non-aromatic amino compound is at least one selected from the group consisting of isophorone diamine, menthane diamine, bis(4-amino-3-methylcyclohexyl)methane, bis(4-aminocyclohexyl)methane, and modifications thereof. Among them, bis(4-amino-3-methylcyclohexyl)methane and bis(4-aminocyclohexyl) methane represented by the chemical formula (2) in an example of the present invention to be described below are particularly preferable. Examples of the modifications of such amines include various modifications such as epoxy modifications, carboxylic acid modifications, urea modifications, modifications with a ketone compound, and modifications with a silane compound, and a modification obtained by modifying any of the above-described alicyclic amino compounds by a known method can be used as appropriate.

Only one type of polyfunctional-amino group-containing compound may be used alone, or two or more types of polyfunctional-amino group-containing compounds may be used in combination.

Examples of the porous particle raw material (a monomer and/or a prepolymer) other than the epoxy monomers and the epoxy prepolymers include: aromatic monovinyl compounds such as styrene monomers including styrene, ethyl styrene, methyl styrene, hydroxy styrene, and chloro styrene; (meth)acrylic esters such as methyl (meth)acrylate, ethyl (meth)acrylate, hydroxyethyl (meth)acrylate, hydroxypropyl (meth)acrylate, butyl (meth) acrylate, 2-ethylhexyl (meth) acrylate, cyclohexyl (meth)acrylate, and glycerin mono(meth)acrylate; (meth)acrylamides such as (meth) acrylamide, dimethyl (meth) acrylamide, and hydroxyethyl (meth)acrylamide; nitriles such as (meth)acrylonitrile; epoxy group-containing compounds such as glycidyl (meth) acrylate, 4,5-epoxy butyl (meth)acrylate, and 9,10-epoxy stearyl (meth)acrylate; and monovinyl monomers of other vinyl esters and vinyl ethers. The porous particles of the present invention may be the following porous particles, for example: porous crosslinked particles obtained by (co)polymerizing one type or two or more types of the porous particle raw materials and then imparting a crosslinked structure to the thus-obtained (co)polymer using a crosslinking agent such as epichlorohydrin, (poly)alkylene glycol diglycidyl ether, or alkylene diisocyanate; porous crosslinked particles obtained by (co)polymerizing one type or two or more types of polyvinyl compounds selected from aromatic polyvinyl compounds such as divinylbenzene and trivinylbenzene, poly(meth)acrylic esters such as (poly) ethylene glycol di(meth)acrylic ester and glycerol di(meth) acrylic ester, polycarboxylic acid polyvinyl esters, polycarboxylic acid polyallyl esters, polyol polyvinyl ethers, polyol polyallyl ethers, butadiene, methylenebisacrylamide, and triallyl isocyanurate; or porous crosslinked particles obtained by copolymerizing one type or two or more types of such polyvinyl compounds with one type or two or more types of the above-described monovinyl monomers. From the viewpoint of industrial productivity, it is preferable that the porous particles of the present invention are porous crosslinked particles obtained by copolymerizing one type or two or more types of polyvinyl compounds with one type or two or more types of monovinyl monomers.

The dispersion medium is not particularly limited, and may be an organic solvent or water. Only one type of dispersion medium may be used, or two or more types of dispersion media may be used in combination. Examples of the organic solvent include: hydrocarbon solvents such as hexane, octane, decane, dodecane, isodecane, cyclohexane, methylcyclohexane, toluene, xylene, ethylbenzene, and cumene; alcohol solvents such as methanol, ethanol, propanol, isopropanol, butanol, isobutanol, hexanol, benzyl alcohol, and cyclohexanol; glycol solvents such as ethylene glycol, diethylene glycol, propylene glycol, dipropylene glycol, methyl cellosolve, ethyl cellosolve, butyl cellosolve, propylene glycol monomethyl ether, propylene glycol monoethyl ether, propylene glycol propyl ether, diglyme, triglyme, dipropylene glycol dimethyl ether, butyl carbitol, butyl triethylene glycol, methyl dipropylene glycol, methyl cellosolve acetate, propylene glycol monomethyl ether acetate, dipropylene glycol butyl ether acetate, and diethylene glycol monobutyl ether acetate; ether solvents such as diethyl ether, dipropyl ether, methyl cyclopropyl ether, tetrahydrofuran, dioxane, and anisole; ketone solvents such as methyl ethyl ketone, diethyl ketone, methyl isobutyl ketone, cyclohexanone, isophorone, and acetophenone; ester solvents such as methyl acetate, ethyl acetate, butyl acetate, propyl acetate, methyl butyrate, ethyl butyrate, caprolactone, methyl lactate, and ethyl lactate; halogenated solvents such as chloroform and dichloroethane; amide solvents such as dimethylformamide, dimethylacetamide, pyrrolidone, and N-methylpyrrolidone, and caprolactam; and dimethyl sulfoxide, sulfolane, tetramethylurea, ethylene carbonate, propylene carbonate, dimethyl carbonate, ethyl carbonate, nitromethane, acetonitrile, nitrobenzene, and dioctyl phthalate. Only one type of organic solvent may be used, or two or more types of organic solvents may be used in combination.

The concentration of the porous particle raw material (a monomer and/or a prepolymer) in the dispersion is not particularly limited, and is, for example, 0.01 to 10,000 g/l, 1 to 5,000 g/l, or 5 to 3,000 g/l with respect to the dispersion medium.

In the porous particle production method according to the present invention, for example, in the dispersion preparation step, the porous particle raw material may be dispersed in the dispersion medium together with a dispersant. The concentration of the dispersant is not particularly limited, and is, for example, 1 to 500 g/l, 2 to 300 g/l, or 3 to 250 g/l with respect to the dispersion medium.

The dispersant may be a surfactant, for example. The surfactant is not particularly limited, and is, for example, an anionic surfactant, a cation surfactant, a nonionic surfactant, or a block copolymer composed of a hydrophilic block and a hydrophobic block, such as, for example, a block copolymer composed of a polyacrylic acid block and a polyacrylic ester block, a block copolymer composed of a polyoxyethylene block and a polyacrylic ester block, or a block copolymer composed of a polyoxyethylene block and a polyoxypropylene block.

Examples of the anionic surfactant include fatty acid salts, sulfuric ester salts of higher alcohols, phosphoric ester salts of fatty alcohols, alkyl aryl sulfonate, and formalin condensates of naphthalene sulfonic acid salts. Examples of the cation surfactant include alkyl primary amine salts, alkyl secondary amine salts, alkyl tertiary amine salts, alkyl quaternary ammonium salts, and pyridinium salts. Examples of the nonionic surfactant include polyoxyethylene alkyl ethers, polyoxyethylene alkyl phenylethers, polyoxyethylene alkyl esters, sorbitan alkyl esters, and polyoxyethylene sorbitan alkyl esters. Examples of the high molecular weight surfactant include partially-saponified polyvinyl alcohols, starch, methylcellulose, carboxymethyl cellulose, hydroxyethyl cellulose, and partially-saponified polymatacrylic acid salts.

By selecting a surfactant to be used, it is possible to control the mean particle size, the particle size distribution, and the state of particle agglutination of the porous epoxy resin particles to be obtained. For example, by using an anionic surfactant, a cationic surfactant, or a nonionic surfactant, it is possible to reduce the mean particle size and to narrow the particle size distribution. Also, by using a high molecular weight surfactant, it is possible to increase the mean particle size and to inhibit the particle agglutination. In particular, when a block copolymer composed of a hydrophilic block and a hydrophobic block is used as a surfactant, emulsification can be achieved by adding a small amount of the surfactant. Accordingly, the viscosity of a solution during a polymerization reaction can be kept low, so that the solution can be stirred easily. Thus, it is preferable to use the block copolymer composed of a hydrophilic block and a hydrophobic block as a surfactant.

Only one type of surfactant may be used, or two or more types of surfactants may be used in combination.

The dispersant may be a block copolymer containing a hydrophobic polymer block and a hydrophilic polymer block, for example. In this case, for example, the porous particle production method according to the present invention may further include a dispersant production step of producing the dispersant, and the dispersant production step may include: a first living radical polymerization step of forming one of the hydrophobic polymer block and the hydrophilic polymer block by living radical polymerization; and a second living radical polymerization step of forming the other one of the hydrophobic polymer block and the hydrophilic polymer block by living radical polymerization after the first living radical polymerization step. The block copolymer (dispersant) and the dispersant production step will be described in detail in the following [2-2. Block copolymer (dispersant) and dispersant production step] section.

In the dispersion preparation step, the dispersion may contain a component(s) other than the porous particle raw material and the dispersant. The other component(s) is not particularly limited. For example, the dispersion may contain a surfactant other than the nonionic surfactant, an antifoaming agent, and/or the like, as long as intended dispersion is not affected by the other component(s).

[2-2. Block Copolymer (Dispersant) and Dispersant Production Step]

The block copolymer (dispersant) and the dispersant production step will be described in detail below.

First, since the block copolymer contains a hydrophobic polymer block and a hydrophilic polymer block, it can be referred to as a "surfactant" in a broad sense, as described above. The block copolymer and the dispersant production step may be the same as those described in JP-A-2015-83688 or may be configured on the basis of or with reference to the descriptions in JP-A-2015-83688, for example. Specifically, the block copolymer and the dispersant production step are as described below, for example.

The block copolymer may be, for example, a diblock copolymer composed of the hydrophobic polymer block (may be referred to simply as "hydrophobic block", "hydrophobic block A", or "A block" hereinafter) and the hydrophilic polymer block (may be referred to simply as "hydrophilic block", "hydrophilic block B", or "B block" hereinafter). The block copolymer may be, for example, a block copolymer obtained by polymerizing addition-polymerizable monomers using: a radical-generating agent; organic iodide as a polymerization initiator compound; and an organic phosphorus compound, an organic nitrogen compound, or an organic oxygen compound as a catalyst.

The content of the A block (hydrophobic block) in the block copolymer molecule is, for example, 5 to 95 mass %, 10 to 90 mass %, 15 to 85 mass %, or 20 to 80 mass %. The content of the B block (hydrophilic block) in the block copolymer molecule is, for example, 5 to 95 mass %, 10 to 90 mass %, 15 to 85 mass %, or 20 to 80 mass %.

Examples of a hydrophobic monomer used as the raw material of the A block (hydrophobic block) include: (meth)acrylates ((meth)acrylic esters) having a hydrophobic group(s); vinyl compounds having a hydrophobic group(s); and allyl compounds having a hydrophobic group(s). Examples of a hydrophilic monomer used as the raw material of the B block (hydrophilic block) include: (meth)acrylates ((meth)acrylic esters) having a hydrophilic group(s); vinyl compounds having a hydrophilic group(s); and allyl compounds having a hydrophilic group(s). For example, the hydrophobic monomer may contain lauryl (meth)acrylate, and the hydrophilic monomer may contain polyethylene glycol methacrylate.

As described above, the dispersant (block copolymer) may have a diblock structure containing a hydrophobic polymer block A and a hydrophilic polymer block B (the dispersant also may be referred to as "A-B diblock polymer" hereinafter). For example, in the dispersion preparation step, the dispersant (block copolymer) is dispersed in the dispersion medium together with the porous particle raw material (containing a monomer and/or a prepolymer). When the porous particle raw material is relatively more hydrophilic than the dispersion medium, the hydrophilic polymer block B is adsorbed onto the porous particle raw material, and surfaces of particles formed by agglutination of the porous particle raw material are coated with the hydrophobic polymer block A, for example. As a result, the hydrophobic polymer block A faces the hydrophobic dispersion medium. On the other hand, when the porous particle raw material is relatively more hydrophobic than the dispersion medium, the hydrophobic polymer block A is adsorbed onto the porous particle raw material, and surfaces of particles formed by agglutination of the porous particle raw material are coated with the hydrophilic polymer block B, for example. As a result, the hydrophilic polymer block B faces the hydrophilic dispersion medium. In the above-described manner, the state where the porous particle raw material is dispersed in the dispersion medium in the form of particles can be obtained. This state also can be referred to as the state where the porous particle raw material is emulsified (suspended) in the dispersion medium, for example. With this configuration, it is possible to improve the dispersion stability of the dispersion before and after polymerization and the storage stability of the dispersion, for example.

The porous particle raw material (containing a monomer and/or a prepolymer) is as described above. For example, the porous particle raw material may contain a radical-polymerizable or thermosetting monomer and/or a radical-polymerizable or thermosetting prepolymer. The monomer and prepolymer may be a hydrophilic monomer and a hydrophilic prepolymer, for example.

Next, the production method of the block copolymer (dispersant) may be, for example, a production method in which, as described above, addition-polymerizable monomers (a hydrophobic monomer and a hydrophilic monomer) are polymerized using: a radical-generating agent; organic iodide as a polymerization initiator compound; and an organic phosphorus compound, an organic nitrogen compound, or an organic oxygen compound as a catalyst. Such a production method is described in JP-A-2015-83688, for example. This production method does not have problems of heavy metals, odor, coloration, cost, etc. Specifically, the production method has the following advantages (1) to (6), for example.

(1) The production method does not use any heavy-metal compound; unlike an ATRP method or a DT method, the production method does not use any heavy-metal compound.

(2) Purification is not essential; removal of heavy metals is necessary in the ATRP method and the DT method, and removal of sulfur compounds is necessary in an RAFT method and a MADIX method.

(3) The production method does not require any expensive special compound and can use relatively low cost materials available on the market, and thus can be carried out at low cost; other methods involving living radical polymerization require the use of special compounds.

(4) The production method requires mild polymerization conditions, and can cause polymerization under conditions similar to those in conventional radical polymerization methods; an NMP method has to be carried out at high temperature, and it is necessary to remove oxygen in the ATRP method.

(5) The production method does not require purification of a monomer or a solvent used therein and can use various monomers, and since monomers having various types of functional groups such as acid groups and amino groups can be used, it is possible to introduce various types of functional groups into a polymer block; in particular, an acid group acts as a catalyst poison and thus cannot be used without being treated in the ATRP method, and methacrylate cannot be polymerized successfully according to the NMP method.

(6) The production method can control the molecular weight and structure, so that a block polymer in a desired binding state can be obtained easily. Besides, the production method can attain very high conversion.

It is to be noted that the above explanation is merely illustrative, and in the present invention, the production method of the block copolymer (dispersant) is not particularly limited. That is, the production method of the block copolymer (dispersant) is not limited to the method described in JP-A-2015-83688 only, and may be any production method.

The hydrophobic monomer constituting the A block is not particularly limited, and examples thereof include aliphatic, alicyclic, and aromatic alkyl (meth)acrylates such as methyl (meth)acrylate, ethyl (meth)acrylate, propyl (meth) acrylate, isopropyl (meth)acrylate, butyl (meth)acrylate, 2-methylpropane (meth) acrylate, t-butyl (meth) acrylate, pentyl (meth)acrylate, hexyl (meth) acrylate, octyl (meth)acrylate, 2-ethylhexyl (meth)acrylate, nonyl (meth)acrylate, decyl (meth)acrylate, isodecyl (meth)acrylate, lauryl (meth)acrylate, tetradecyl (meth)acrylate, octadecyl (meth)acrylate, behenyl (meth)acrylate, isostearyl (meth)acrylate, cyclohexyl (meth) acrylate, t-butylcyclohexyl (meth)acrylate, isobornyl (meth)acrylate, 2,2,4-trimethylcyclohexyl (meth) acrylate, cyclodecyl (meth) acrylate, cyclodecylmethyl (meth)acrylate, benzyl (meth)acrylate, t-butyl benzotriazole phenylethyl (meth)acrylate, phenyl (meth)acrylate, naphthyl (meth)acrylate, and allyl (meth)acrylate. In particular, alkyl (meth)acrylates having a long alkyl group, such as lauryl (meth)acrylate, are preferable. Only one type of hydrophobic monomer may be used, or two or more types of hydrophobic monomers may be used in combination.

The hydrophilic monomer constituting the B block is not particularly limited, and may be a monomer having a polyglycol group(s), for example. Specific examples of the monomer having a polyglycol group include: mono(meth) acrylates of polyalkylene glycols, such as poly(n=2 or more)ethylene glycol mono(meth)acrylate, poly(n=2 or more)propylene glycol mono(meth)acrylate, poly(n=2 or more)tetramethylene glycol mono(meth)acrylate, mono (meth)acrylate of a mono or poly(n=2 or more)ethylene glycol mono or poly(n=2 or more)propylene glycol random copolymer, mono(meth)acrylate of a mono or poly(n=2 or more)ethylene glycol mono or poly(n=2 or more)propylene glycol block copolymer; and mono(meth)acrylates of (polyalkylene)glycol monoalkyls, alkylenes, alkyne ethers and esters, such as (poly)ethylene glycol monomethyl ether (meth)acrylate, (poly)ethylene glycol monooctyl ether (meth)acrylate, (poly)ethylene glycol monolauryl ether (meth)acrylate, (poly)ethylene glycol monostearyl ether (meth)acrylate, (poly)ethylene glycol monooleyl ether (meth)acrylate, (poly)ethylene glycol monostearate ester (meth) acrylate, (poly)ethylene glycol monononyl phenylether (meth)acrylate, (poly)propylene glycol monomethyl ether (meth)acrylate, (poly)propylene glycol monoethyl ether (meth)acrylate, (poly)propylene glycol monooctyl ether (meth)acrylate, (poly)propylene glycol monolauryl ether (meth)acrylate, and (poly)ethylene glycol (poly)propylene glycol monomethyl ether (meth)acrylate. In particular, poly(n=6 or more)ethylene glycol mono(meth)acrylates are desirable. n indicates the degree of polymerization in the polyglycol group. Only one type of hydrophilic monomer may be used, or two or more types of hydrophilic monomers may be used in combination.

The block copolymer (dispersant) may be composed of the hydrophobic polymer block A (A block) and the hydrophilic polymer block B (B block) only, or a component(s) other than the A block and the B block further may be contained (copolymerized) in the block copolymer (dispersant).

Examples of a monomer that can be copolymerized without changing the basic properties of the A block and the B block include conventionally known monomers including: vinyl monomers such as styrene, vinyltoluene, vinylhydroxybenzene, chloromethylstyrene, vinylnaphthalene, vinylbiphenyl, vinylethylbenzene, vinyldimethylbenzene, α-methyl styrene, ethylene, propylene, isoprene, butene, butadiene, 1-hexene, cyclohexene, cyclodecene, dichloroethylene, chloroethylene, fluoroethylene, tetrafluoroethylene, acrylonitrile, methacrylonitrile, vinyl acetate, vinyl propionate, isocyanato dimethyl methane isopropenyl benzene, phenylmaleimide, cyclohexylmaleimide, and hydroxymethylstyrene; and hydroxy group-containing monomers such as mono(meth)acrylic esters of alkylene glycol, including 2-hydroxyethyl (meth)acrylate, 2-hydroxypropyl (meth) acrylate, 3-hydroxypropyl (meth)acrylate, 4-hydroxybutyl (meth)acrylate, 6-hydroxyhexyl (meth) acrylate, cyclohexanedimethanol mono(meth)acrylate, and cyclohexanediol mono(meth)acrylate. Examples of the monomer further include: a polyester mono(meth)acrylic ester obtained by ring-opening polymerization of the above-described (poly)alkylene glycol mono(meth)acrylic ester of (meth)acryloyloxy ethyl mono or poly(n=2 or more)caprolactone or lactone such as ε-caprolactone or γ-butyrolactone; ester (meth)acrylate obtained by reacting the above-described (poly)alkylene glycol mono(meth)acrylic ester of 2-(meth)acryloyloxy ethyl-2-hydroxyethyl phthalate or 2-(meth)acryloyloxy ethyl-2-hydroxyethyl succinate with a dibasic acid to cause half esterification and then reacting the other carboxyl group with an alcohol or alkylene glycol; mono(meth)acrylates of polyfunctional hydroxy group-containing compounds having three or more hydroxy groups, such as glycerol mono(meth)acrylate and dimethylolpropane mono(meth)acrylate; halogen-containing (meth)acrylates such as 3-chloro-2-hydroxypropyl (meth)acrylate, octafluorooctyl (meth)acrylate, and tetrafluoroethyl (meth)acrylate; monomers that absorb ultraviolet rays, such as 2-(4-benzoxy-3-hydroxyphenoxy)ethyl (meth)acrylate and 2-(2'-hydroxy-5-(meth)acryloyloxyethylphenyl)-2H-benzotriazole (these monomers may be copolymerized especially when improvement in light resistance of a dye is desired); and acrylates with their α-positions being substituted by hydroxymethyl, such as ethyl-α-hydroxymethyl acrylate.

The molecular weight of the block copolymer (dispersant) is not particularly limited, and the styrene-equivalent number-average molecular weight determined by gel permeation chromatography (referred to as "GPC" hereinafter) (hereinafter, the term "number-average molecular weight" means the styrene-equivalent number-average molecular weight determined by GPC and may be referred to simply as "molecular weight") is, for example 1,000 or more, 1,500 or more, 2,000 or more, or 3,000 or more, and, for example, 300,000 or less, 100,000 or less, or 50,000 or less. The molecular weight is in the range from, for example, 1,000 to 300,000, preferably 1,500 to 100,000, more preferably 2,000 to 50,000, and still more preferably 3,000 to 50,000. From the viewpoint of the dispersion stability of the porous particle raw material in the dispersion medium, it is preferable that the molecular weight of the block copolymer (dispersant) is 1,000 or more. From the viewpoint of the solubility of the block copolymer (dispersant) in the dispersion medium, it is preferable that the molecular weight of the block copolymer (dispersant) is 300,000 or less. If the molecular weight of the block copolymer (dispersant) is too high, the porous particle raw material may not be dispersed owing to agglutination of the dispersant and too strong entanglement of molecules of the dispersant in the dispersion medium.

In the block copolymer (dispersant), the polydispersity index (referred to as "PDI" hereinafter), which is the ratio of the weight-average molecular weight to the number-average molecular weight, is not particularly limited. In living radical polymerization, a polymeric dispersant having a very small PDI (up to 1.3) may be used. However, in the present invention, the important thing is that the block copolymer (dispersant) has the above-described block structure, and the PDI is not deeply involved in the present invention. However, when the PDI is too broad, it means that the molecular weight of polymers contained in the block copolymer (dispersant) ranges from large to small, so that phenomena other than the phenomenon that occurs in the above-described molecular weight range may occur. On this account, too broad PDI is not preferable. In the block copolymer (dispersant) used in the present invention, the PDI preferably is 2.0 or less, more preferably 1.8 or less.

Next, the mass ratio between the hydrophobic block and the hydrophilic block in the block copolymer (dispersant) is not particularly limited, and is as described above, for example. By controlling the mass ratio between the hydrophobic block and the hydrophilic block appropriately, the interface between the porous particle raw material and the dispersion medium can be maintained in a suitable state in the porous particle production method according to the present invention, for example. With this configuration, for example, the state where the porous particle raw material is dispersed in the dispersion medium in the form of particles can be maintained, whereby the substantially spherical porous particles of the present invention can be produced. Also, by controlling the mass ratio between the hydrophobic block and the hydrophilic block appropriately, the ratio between the hydrophilic substance and the hydrophobic substance can be controlled in a suitable state at the interface between the porous particle raw material and the dispersion medium, for example. If either one of the hydrophilic substance and the hydrophobic substance is present disproportionately at the interface, for example, a skin layer may be formed by polymerization or the like of the substance. The through holes on the surface of the porous particle are likely to be closed by this skin layer. However, by controlling the ratio between the hydrophilic substance and the hydrophobic substance in a suitable state at the interface, it is possible to prevent the formation of the skin layer. It is to be noted, however, that the above explanations are merely illustrative and do not limit the present invention.

Next, the polymerization method (production method) for obtaining the block copolymer (dispersant) used in the present invention will be described. This polymerization method is not particularly limited, and as described above, it may be a method for polymerizing addition-polymerizable monomers (a hydrophobic monomer and a hydrophilic monomer) using: a radical-generating agent; organic iodide as a polymerization initiator compound; and an organic phosphorus compound, an organic nitrogen compound, or an organic oxygen compound as a catalyst, for example. This polymerization method does not require the use of any metal compound or ligand, and also does not require the use of any special compound such as nitroxide, a dithiocarboxylic acid ester, or xanthate. This polymerization method is living radical polymerization that can be carried out easily merely by additionally using an initiator compound, which is an organic iodide, and a catalyst in radical polymerization that uses conventional addition-polymerizable monomers and a radical-generating agent as a polymerization initiator.

In the polymerization method, the reaction proceeds through a reaction mechanism represented by the following general reaction formula 1.

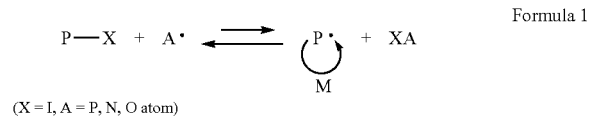

Formula 1

(X = I, A = P, N, O atom)

This reaction is considered to be a reversible activation reaction of a dormant species Polymer-X (P-X) to a propagating radical. It is considered that this polymerization mechanism proceeds in the following manner, although the polymerization mechanism may vary depending on the type of the catalyst. In Formula 1, P. generated from a polymerization initiator reacts with XA, whereby a catalyst A. is generated in situ. A. acts as an activator of P-X. By this catalytic action, P-X is activated at a high frequency.

More specifically, in the presence of an initiator compound having iodine (X) bound thereto, a radical generated from the polymerization initiator abstracts active hydrogen or an active halogen atom in the catalyst to form a catalytic radical A. Subsequently, this A. abstracts X in the initiator compound to form XA, and the initiator compound then serves as a radical. A monomer polymerizes with the radical, and immediately abstracts X from XA, whereby a termination reaction is prevented. Further, A. abstracts X at the terminus when subjected to heat or the like, whereby XA and the terminal radical are provided. A monomer reacts with the terminal radical to donate X thereto immediately, thereby stabilizing the terminal radical. The polymerization proceeds by repeating the above process, so that the molecular weight and the structure can be controlled. However, in some cases, a side reaction such as a bimolecular termination reaction or disproportionation may occur.

The initiator compound used to initiate the living radical polymerization is not particularly limited, and may be a conventionally known organic iodide. Specific examples of the initiator compound include: methyl iodide, ethyl iodide, propyl iodide, isopropyl iodide, butyl iodide, and t-butyl iodide; alkyl iodides such as iodophenylmethane, iododiphenylmethane, iodotriphenylmethane, 2-iodo-1-phenylethane, 1-iodo-1-phenylethane, 1-iodo-1,1-diphenylethane, and diiodomethane; iodine atom-containing organic halides such as iodo dichloromethane, iodochloromethane, iodotrichloromethane, and iododibromomethane; iodinated alcohols such as 1-iodoethanol, 1-iodopropanol, 2-iodopropanol, 2-iodo-2-propanol, 2-iodo-2-methylpropanol, 2-phenyl-1-iodoethanol, and 2-phenyl-2-iodoethanol; ester compounds of these iodinated alcohols with carboxylic acid compounds such as acetic acid, butyric acid, and fumaric acid; iodinated carboxylic acids such as iodoacetic acid, α-iodopropionic acid, α-iodobutyric acid, α-iodoisobutyric acid, α-iodovaleric acid, α-iodoisovaleric acid, α-iodocaproic acid, α-iodophenylacetic acid, α-iododiphenylacetic acid, α-iodo-α-phenylpropionic acid, α-iodo-β-phenylpropionic acid, β-iodopropionic acid, β-iodobutyric acid, β-iodoisobutyric acid, β-iodovaleric acid, β-iodoisovaleric acid, β-iodocaproic acid, β-iodophenylacetic acid, β-iododiphenylacetic acid, β-iodo-α-phenylpropionic acid, and β-iodo-β-phenylpropionic acid; esterified products of these iodinated carboxylic acids with methanol, ethanol, phenol, or benzyl alcohol, and further, esterified product of these iodinated carboxylic acids with the above-described iodinated alcohols; acid anhydrides of these iodinated carboxylic acids; acid anhydrides of chlorides, bromides, and the like of these iodinated carboxylic acids; and cyano group-containing iodides such as iodoacetonitrile, 2-cyano-2-iodopropane, 2-cyano-2-iodobutane, 1-cyano-1-iodocyclohexane, and 2-cyano-2-iodovaleronitrile. Also, it is possible to use a bifunctional initiator compound having two iodine atoms. Examples of the bifunctional initiator compound include compounds obtained by reacting an iodinated carboxylic acid (such as 1,2-diiodo ethane, 1,2-diiodotetrafluoroethane, 1,2-diiodotetrachloroethane, 1,2-diiodo-1-phenylethane, or the above-described α-iodoisobutyric acid) with a diol such as ethylene glycol or a diamine such as hexamethylenediamine. Although two different Japanese terms are used to indicate "iodo", they should be interpreted as interchangeable with each other and both indicate "iodide". The same applies hereinafter. Only one type of initiator compound may be used, or two or more types of initiator compounds may be used in combination.

As these compounds, commercially available products may be used as they are, or these compounds can be obtained by conventionally known methods, for example. For example, the organic iodide used in the present invention can be obtained by reacting an azo compound such as azobisisobutyronitrile with an iodine, or by causing a halogen exchange reaction of an organic halide containing, instead of iodine in the above-described organic iodides, another halogen atom such as bromide or chloride, using an iodide salt such as quaternary ammonium iodide or sodium iodide. The method for obtaining the organic iodide is not particularly limited.

The catalyst is, for example, an organic phosphorus compound, organic nitrogen compound, or organic oxygen compound that abstracts an iodine atom in the initiator compound to form a radical. Preferably, the catalyst is at least one selected from: organic phosphorus compounds such as halogenated phosphorus/phosphite compounds containing an iodine atom(s) and phosphonate compounds; organic nitrogen compounds such as imide compounds and hydantoin compounds; and organic oxygen compounds such as phenol compounds, iodo oxyphenyl compounds, and vitamins. These compounds are not particularly limited, and specific examples thereof are as follows. The phosphorus compound are halogenated phosphorus/phosphite compounds containing an iodine atom(s) and phosphonate compounds, and examples thereof include dichloroiodophosphorus, dibromoiodophosphorus, phosphorus triiodide, dimethyl phosphite, diethyl phosphite, dibutyl phosphite, diperfluoroethyl phosphonate, diphenyl phosphite, dibenzyl phosphite, bis(2-ethylhexyl)phosphite, bis(2,2,2-trifluoroethyl)phosphite, diallyl phosphite, ethylene phosphite, ethoxyphenyl phosphonate, phenylphenoxy phosphonate, ethoxymethyl phosphonate, and phenoxymethyl phosphonate. The nitrogen compounds are imide compounds and hydantoin compounds, and examples thereof include succinimide, 2,2-dimethylsuccinimide, α,α-dimethyl-β-methylsuccinimide, 3-ethyl-3-methyl-2,5-pyrrolidinedione, cis-1,2,3,6-tetrahydrophthalimido, α-methyl-α-propylsuccinimide, 5-methylhexahydroisoindol-1,3-zione, 2-phenylsuccinimide, α-methyl-α-phenylsuccinimide, 2,3-diacetoxsuccinimide, maleimide, phthalimido, 4-methylphthalimido, N-chlorophthalimido, N-bromophthalimido, N-bromophthalimido, 4-nitrophthalimido, 2,3-naphthalenecarboxyimide, pyromellitdiimide, 5-bromoisoindol-1,3-zione, N-chlorosuccinimide, N-bromosuccinimide, N-iodosuccinimide, hydantoin, and diiodohydantoin. The oxygen compounds are: phenol compounds, which are phenolic hydroxy groups having a hydroxy group on the aromatic ring; iodo oxyphenyl compounds, which are iodides of the phenolic hydroxy groups; and vitamins. Examples thereof include: polymers obtained by polymerizing phenols such as phenol, hydroquinone, methoxyhydroquinone, t-butylphenol, t-butylmethylphenol, catechol, resorcinol, di-t-butylhydroxytoluene, dimethylphenol, trimethylphenol, di-t-butylmethoxyphenol, and hydroxystyrene; and polymer fine particles carrying the hydroxyphenyl groups thereof. They are added as a polymerization inhibitor for storage of monomers. Thus, a similar effect also can be obtained by using commercially available monomers without purifying them. Examples of the iodo oxyphenyl compounds include thymol diiodide. Examples of the vitamins include vitamin C and vitamin E.

The amount of the catalyst is not particularly limited. For example, the number of moles of the catalyst is less than the number of moles of the polymerization initiator. If the number of moles of the catalyst is too large, there is a risk that the polymerization may be controlled too much to inhibit the proceeding of the polymerization.

Next, the polymerization initiator used in the present invention is not particularly limited, and may be, for example, a conventionally known polymerization initiator used commonly, such as an organic peroxide or an azo compound. Specific examples of the polymerization initiator include benzoyl peroxide, dicumyl peroxide, diisopropyl peroxide, di-t-butyl peroxide, t-butyl peroxybenzoate, t-hexyl peroxybenzoate, t-butylperoxy-2-ethyl hexanoate, t-hexylperoxy-2-ethyl hexanoate, 1,1-bis(t-butylperoxy)3,3,5-trimethyl cyclohexane, 2,5-dimethyl-2,5-bis(t-butylperoxy)hexyl-3,3-isopropyl hydroperoxide, t-butyl hydroperoxide, dicumyl hydroperoxide, acetyl peroxide, bis(4-t-butylcyclohexyl)peroxy dicarbonate, isobutyl peroxide, 3,3,5-trimethyl hexanoyl peroxide, lauryl peroxide, 1,1-bis(t-butylperoxy)3,3,5-trimethyl cyclohexane, 1,1-bis(t-hexylperoxy)3,3,5-trimethyl cyclohexane, 2,2'-azobis(isobutyronitrile), 2,2'-azobis(2,4-dimethylvaleronitrile), 2,2'-azobis(isobutyrate), and 2,2'-azobis(methoxy dimethylvaleronitrile). Only one type of polymerization initiator may be used, or two or more types of polymerization initiators may be used in combination.

The amount of the polymerization initiator to be used is not particularly limited, and may be such that, for example, the number of moles of the polymerization initiator is 0.001 to 0.1 times, more preferably 0.002 to 0.05 times the number of moles of the monomers. When the amount of the polymerization initiator to be used is too small, polymerization may be inadequate. When the amount of the polymerization initiator to be used is too large, the resultant polymer may be composed of the addition-polymerized monomers only.

As described above, by causing polymerization using at least an initiator compound, which is an organic iodide, addition-polymerizable monomers, a polymerization initiator, and a catalyst, it is possible to obtain the block copolymer (dispersant) used in the present invention. Although the polymerization may be bulk polymerization performed without using an organic solvent, it is preferable that the polymerization is solution polymerization performed using a solvent. The organic solvent to be used is not particularly limited as long as it dissolves the organic iodide, the catalyst, the addition-polymerizable monomers, and the polymerization initiator used in the present invention. Examples of the organic solvent include: hydrocarbon solvents such as hexane, octane, decane, isodecane, cyclohexane, methylcyclohexane, toluene, xylene, ethylbenzene, and cumene; alcohol solvents such as methanol, ethanol, propanol, isopropanol, butanol, isobutanol, hexanol, benzyl alcohol, and cyclohexanol; glycol solvents such as ethylene glycol, diethylene glycol, propylene glycol, dipropylene glycol, methyl cellosolve, ethyl cellosolve, butyl cellosolve, propylene glycol monomethyl ether, propylene glycol monoethyl ether, propylene glycol propyl ether, diglyme, triglyme, dipropylene glycol dimethyl ether, butyl carbitol, butyl triethylene glycol, methyl dipropylene glycol, methyl cellosolve acetate, propylene glycol monomethyl ether acetate, dipropylene glycol butyl ether acetate, and diethylene glycol monobutyl ether acetate; ether solvents such as diethyl ether, dipropyl ether, methyl cyclopropyl ether, tetrahydrofuran, dioxane, and anisole; ketone solvents such as methyl ethyl ketone, diethyl ketone, methyl isobutyl ketone, cyclohexanone, isophorone, and acetophenone; ester solvents such as methyl acetate, ethyl acetate, butyl acetate, propyl acetate, methyl butyrate, ethyl butyrate, caprolactone, methyl lactate, and ethyl lactate; halogenated solvents such as chloroform and dichloroethane; amide solvents such as dimethylformamide, dimethylacetamide, pyrrolidone, N-methylpyrrolidone, and caprolactam; and dimethyl sulfoxide, sulfolane, tetramethylurea, ethylene carbonate, propylene carbonate, dimethyl carbonate, ethyl carbonate, nitromethane, acetonitrile, nitrobenzene, and dioctyl phthalate. Only one type of organic solvent may be used, or two or more types of organic solvents may be used in combination.

The solid content (monomer concentration) in a polymerization solution is not particularly limited, and is, for example, 5 to 80 mass %, preferably 20 to 60 mass %. From the viewpoint of achieving polymerization smoothly, it is preferable that the monomer concentration is not too low. Also, from the viewpoint of preventing the viscosity of the polymerization solution from being too high to make a stirring operation difficult or to lower the conversion, it is preferable that the monomer concentration is not too high.

The polymerization temperature is not particularly limited, and is 0° C. to 150° C., more preferably 30° C. to 120° C. The polymerization temperature is adjusted according to the half-life of the type of the polymerization initiator. The polymerization time is not particularly limited. Preferably, polymerization is performed until all the monomer units are polymerized. The polymerization time is, for example, 0.5 to 48 hours, and a practical polymerization time preferably is 1 to 24 hours, more preferably 2 to 12 hours.

The atmosphere in which the polymerization reaction is performed is not particularly limited. For example, the polymerization may be performed in the air (in other words, oxygen may be present at an ordinary concentration in a system) or, when necessary, the polymerization may be performed in a nitrogen or argon gas stream in order to remove oxygen. The materials used in the polymerization may be subjected to distillation or a treatment using an active carbon or alumina to remove impurities therefrom. Alternatively, commercially available products may be used as they are. Polymerization may be performed under light shielding conditions. Also, there is no problem to perform polymerization in a transparent container such as a glass container.

The operation procedure and mechanism of the production method (polymerization method) of the block copolymer (dispersant) are, for example, as described below. First, using a monofunctional organic iodide as an initiator compound, an addition-polymerizable monomer having at least an acid group(s) is polymerized by the above-described method to obtain one polymer block (referred to as "A block"). The terminus of this polymer is stabilized by being substituted with an iodine group. Thus, it is possible to start polymerization again by adding a monomer again and applying heat or the like to cause dissociation or by further adding a small amount of a radical initiator.

The thus-obtained A block is collected and purified, and is dissolved in the organic solvent again. Using this A block as an initiator compound, polymerization is caused by adding a subsequent monomer (preferably also adding a catalyst and a polymerization initiator). As a result, iodine at the terminus of the polymer is dissociated, whereby polymerization starts again. Thus, a diblock polymer composed of the A block and the B block bound to each other can be obtained. The block copolymer (dispersant) also can be obtained by, after the formation of the A block, adding a B block monomer (preferably also adding the catalyst and the polymerization initiator) without taking out the polymer to perform polymerization.

The A-B diblock polymer (the block copolymer) may be obtained in the same manner by generating the blocks in reverse order, namely, by polymerizing the B block monomer to form a hydrophilic polymer first and then polymerizing a monomer containing at least a monomer unit(s) having a hydrophobic group(s).

In the polymerization used in the present invention, the molecular weight of a polymer can be controlled by adjusting the amount of an initiator compound, for example. More specifically, for example, by setting the number of moles of a monomer relative to the number of moles of the initiator compound, it is possible to control the molecular weight to any desired value or to roughly control the size of the molecular weight. For example, when polymerization is caused using 1 mol of an initiator compound and 500 mol of a monomer with a molecular weight of 100, the theoretical molecular weight of the resultant polymer is 1×100× 500=50,000. That is, the set molecular weight can be calculated according to the following formula.

[1 mol of initiator compound×molecular weight of monomer×molar ratio of the initiator compound to the monomer]

However, the polymerization method used in the present invention may involve a side reaction such as bimolecular termination or disproportionation, so that the above-described theoretical molecular weight may not be obtained. Although it is preferable to obtain a polymer without causing these side reactions, the molecular weight may be increased as a result of coupling or may be decreased as a result of termination. Further, the conversion does not have to be 100%. The remaining monomer may be removed by evaporation or may be removed at the time of precipitating the block polymer. Alternatively, after the desired block polymer is obtained, polymerization of the remaining monomer may be completed by adding a polymerization initiator and a catalyst. The polymerization method is not limited as long as the diblock polymer used in the present invention is generated or contained in the reaction product. Also, there is no problem if the respective block polymer units are contained in the reaction product. The block copolymer (dispersant) preferably contains at least 50 mass %, more preferably at least 80 mass % of the block polymer of the present invention. Although the above-described side reactions result in broader PDI, the PDI is not particularly limited, and preferably is 2.0 or less, more preferably 1.8 or less.

By causing polymerization using at least addition-polymerizable monomers, a polymerization initiator, and a catalyst with an organic iodide as an initiator compound as described above, it is possible to obtain a diblock polymer, which is the block copolymer (dispersant) used in the present invention. It is to be noted, however, that, as described above, this production method (polymerization method) may be selected freely, and the block copolymer (dispersant) used in the present invention may be produced by any method.

[2-3. Production of Porous Particles by Polymerization]

The porous particle production method according to the present invention can be carried out specifically in the following manner, for example. In the following, an example where the production method uses a porous particle raw material containing a thermosetting monomer and/or a thermosetting prepolymer will be described mainly. In particular, an example where the porous particle raw material contains an epoxy monomer and/or an epoxy prepolymer as the thermosetting monomer and prepolymer will be described. It should be noted that, as described above, the porous particle raw material is not particularly limited, and may be selected freely.

First, a dispersion is prepared by dispersing a porous particle raw material containing a monomer and/or a prepolymer in a dispersion medium to which the block copolymer (dispersant) has been added previously (the dispersion preparation step). The porous particle raw material is as described above. The dispersion preparation step specifically is performed by, for example, mixing a thermosetting composition containing at least a solvent serving as a porogen with a hydrophobic organic solvent (dispersion medium) to which the block copolymer (dispersant) has been added previously to disperse the thermosetting composition in the hydrophobic organic solvent in the form of particles. The thermosetting composition (porous particle raw material) is, for example, an epoxy resin raw material composition containing an epoxy resin raw material (an epoxy monomer and/or an epoxy prepolymer), a curing agent, and a porogen. Thereafter, the polymerization step is performed by heating the dispersion, for example. Then, epoxy resin porous particles are obtained through polymerization (curing) (the polymerization step). Thereafter, the porogen, the solvent, the unreacted substances, and the like are removed from the porous particles (particulate cured product), when necessary.

The epoxy monomer and epoxy prepolymer as the raw material are as described above. Among the above-described epoxy monomers and epoxy prepolymers, epoxy monomers and epoxy prepolymers having an epoxy equivalent of 600 or less and dissolvable in a porogen are particularly preferable.

The curing agent used in the porous particle production method of the present invention is not particularly limited, and examples thereof include amines, polyamideamines, acid anhydrides, and phenol curing agents. Among the above-described curing agents, polyfunctional-amino group-containing compounds are as described above, for example. More specifically, examples of the polyfunctional-amino group-containing compounds include meta-phenylenediamine, diaminodiphenylmethane, diaminodiphenylsulfone, bis(4-amino-3-methylcyclohexyl)methane, bis(4-aminocyclohexyl)methane, and aliphatic polyamideamines each composed of a polyamine and a dimer acid. In the present invention, it is preferable to use a curing agent that can react with an epoxy resin to form a hydroxy group, thereby imparting hydrophilicity to a porous material to be obtained or a curing agent that has a function of chemically modifying the porous material afterward.

In the porous particle production method according to the present invention, a curing accelerator also may be used. The curing accelerator is not particularly limited, and may be any known compound. Examples of the curing accelerator that can be used suitably include: tertiary amines such as triethylamine and tributylamine; and imidazoles such as 2-phenol-4-methylimidazole, 2-ethyl-4-methylimidazole, and 2-phenol-4,5-dihydroxymethylimidazole.

In the present invention, the term "porogen" means an inactive solvent or an inactive solvent-containing mixture serving as a pore forming agent. A porogen is present in a polymerization reaction that forms a porous polymer at a certain stage of polymerization. By removing the porogen from the reaction mixture at a predetermined stage, a porous epoxy resin cured product having a three-dimensional network structure with mutually communicating spaces is obtained.

In the present invention, the porogen is, for example, a solvent in which the porous particle raw material and the curing agent can be dissolved and reaction-induced phase separation can be caused after the polymerization of the porous particle raw material and the curing agent. Examples of the porogen include: cellosolves such as methyl cellosolve and ethyl cellosolve; esters such as ethylene glycol monomethyl ether acetate and propylene glycol monomethyl ether acetate; and glycols such as polyethylene glycol and polypropylene glycol. Among them, polyethylene glycol, methyl cellosolve, ethyl cellosolve, ethylene glycol monomethyl ether acetate, and propylene glycol monomethyl ether acetate each having a molecular weight of about 200 to about 20,000 are preferable, and polyethylene glycol and propylene glycol monomethyl ether acetate each having a molecular weight of about 200 to about 20,000 are particularly preferable. Only one type of porogen may be used, or two or more types of porogens may be used in combination.

In the present invention, it is desirable to use, as a porogen, polyalkylene glycol or a polyalkylene glycol derivative having a hydroxy group(s) and a hydroxyl value of 100 (mg KOH/g) or more, for example. When the hydroxyl value is less than 100 (mg KOH/g), the viscosity is too high. As a result, it may be difficult for a porous epoxy resin cured product to have a sufficiently large diameter or the effect of imparting hydrophilicity to the porous epoxy resin cured product may be deteriorated. The reason for this is considered as follows: since the amount of the hydroxy group on the surface of the porous epoxy resin cured product is closely related to the hydroxyl equivalent of the porogen, the amount of the hydroxy group appearing on the surface of the epoxy resin cured product reduces as the hydroxyl value of the porogen becomes smaller, whereby the hydrophilicity of the surface is deteriorated. The porogen can be used not only for the synthesis of epoxy resin porous particles but also for the synthesis of porous particles made of other materials.

The thermosetting composition (porous particle raw material) is, for example, an epoxy resin raw material composition containing an epoxy resin raw material (an epoxy monomer and/or an epoxy prepolymer), a curing agent, and a porogen, as described above. This thermosetting composition (porous particle raw material) can be prepared by, for example, homogenously mixing the epoxy resin raw material (an epoxy monomer and/or an epoxy prepolymer) and the curing agent in the porogen.

The contents of the epoxy resin raw material (for example, polyfunctional-epoxy group-containing compound) and the curing agent (for example, polyfunctional-amino group-containing compound) in the thermosetting composition preferably are set so that, with respect to 1 equivalent of the epoxy group in the epoxy resin raw material, 0.8 to 1.2 equivalents, in particular, 0.9 to 1.1 equivalents of the functional group (e.g., an amino group) in the curing agent is present, for example. For example, by setting the equivalent ratio of the epoxy resin raw material so as to be not less than the lower limit, a porous epoxy resin to be obtained can have an improved crosslinking density and thus tends to exhibit improved mechanical strength, heat resistance, solvent resistance, etc. On the other hand, by setting the equivalent ratio of the epoxy resin raw material so as to be not more than the upper limit, the amount of unreacted curing agent can be reduced and the curing agent can be prevented from remaining in the porous epoxy resin in an unreacted state. Thus, the crosslinking density tends to be improved.

The content of the solvent serving as a porogen in the thermosetting composition affects the pore diameter, the pore distribution, etc. of porous epoxy resin particles to be obtained, for example. When the content of the porogen is high, the porous epoxy resin particles tend to have a large pore diameter. On the other hand, when the content of the porogen is low, the porous epoxy resin particles tend to have a small pore diameter. Further, when the content of the porogen is high, the porous epoxy resin particles tend to exhibit broad pore distribution. On the other hand, when the content of the porogen is low, the porous epoxy resin particles tend to exhibit sharp pore distribution.

The content of the solvent serving as a porogen in the thermosetting composition generally is set so that the amount of the solvent is preferably 50 to 300 wt %, more preferably 100 to 200 wt % with respect to the total amount of a polyfunctional-epoxy group-containing compound and a polyfunctional-amino group-containing compound contained in the thermosetting composition. When the content of the porogen is not less than the lower limit, a pore structure with a higher porosity can be formed. On the other hand, when the content of the porogen is not more than the upper limit, the porosity of the porous epoxy resin to be obtained can be controlled so as to be in a suitable range, so that the porous epoxy resin tends to have improved mechanical strength.

The thermosetting composition may further contain a curing accelerator. The curing accelerator is not particularly limited, and examples thereof are as described above.

The thermosetting composition may further contain a reaction raw material compound(s) other than the epoxy resin raw material and the curing agent. A reaction raw material compound that can be used in an addition polymerization reaction together with the epoxy resin raw material and the curing agent is not particularly limited as long as, for example, it can be addition-polymerized together with the epoxy resin raw material and the curing agent. For example, as the reaction raw material compound(s), one type or two or more types of monomers and prepolymers given above as examples of the polymer raw material other than epoxy resins can be used. In order to obtain the intrinsic characteristics of the porous epoxy resin, such as the impact resistance, chemical resistance, durability, handleability, and productivity, effectively, the amount of the reaction raw material compound(s) other than the epoxy resin raw material and the curing agent preferably is 30 wt % or less, particularly preferably 0 to 15 wt %, with respect to the total amount of all the reaction raw material compounds.

The method for preparing the thermosetting composition is not particularly limited, and the following method may be employed: mixing a polyfunctional-epoxy group-containing compound, a polyfunctional-amino group-containing compound, and a porogen together at an ordinary temperature or while heating; or adding a mixture of a polyfunctional-epoxy group-containing compound and a polyfunctional-amino group-containing compound to a porogen, and then mixing them together or dissolving the mixture in the porogen at an ordinary temperature or while heating.

Next, in the dispersion preparation step, the porous particle raw material (thermosetting composition) can be dispersed in the form of particles by stirring the dispersion medium while applying sufficient shear force, for example. In this case, a suitable method can be selected in consideration of the size of the particles and the particle size distribution. For example, the method for dispersing the porous particle raw material (thermosetting composition) may be a method that can apply sufficient shear force. More specifically, for example, it is possible to use not only devices with stirring blades in various shapes (such as propeller-type, paddle-type, turbine-type, or screw-type stirring blades) but also known methods such as the use of a planetary centrifugal mixer or a "vortex mixer" that stirs liquid contained in a test tube by rotating the bottom of the test tube at a high speed, stirring utilizing ultrasonic waves, or a membrane emulsification method. It is preferable to select a method that can provide uniform particle diameters to the extent possible.

In the dispersion preparation step, as described above, the thermosetting composition may be mixed with a hydrophobic organic solvent (dispersion medium) to which the block copolymer (dispersant) has been added previously to disperse the thermosetting composition in the hydrophobic organic solvent in the form of particles, for example. In the hydrophobic organic solvent (dispersion medium) to which the block copolymer (dispersant) has been added previously, the concentration of the block copolymer (dispersant) is not particularly limited, and is, for example, 1 to 500 g/l, 2 to 300 g/l, or 3 to 250 g/l, as described above. By setting the concentration of the block copolymer so as to be not less than the lower limit, the particle diameter can be controlled easily and agglutination during the polymerization can be inhibited. On the other hand, by setting the concentration of the block copolymer so as to be not more than the upper limit, it is possible to inhibit the occurrence of foaming and the increase in viscosity during the polymerization, so that the porous particles can be produced easily. Then, as described above, in the state where the thermosetting composition is dispersed in the hydrophobic organic solvent in the form of particles, i.e., in the state where water-in-oil type emulsion is formed, a subsequent polymerization step can be performed.

In the polymerization step of polymerizing the porous particle raw material in the dispersion, the amount of the dispersant (e.g., the block copolymer or surfactant) to be used is not particularly limited, and may be about 1 to 20 wt % or about 2 to 10 wt % with respect to the total amount of the epoxy resin raw material, the curing agent, and the porogen, for example. The amount of the dispersant to be used affects the mean particle size and the particle size distribution of porous particles to be obtained and particle agglutination, for example. When the amount of the dispersant to be used is large, it is possible to control the mean particle size and the particle size distribution of porous particles to be obtained and particle agglutination. When the amount of the dispersant to be used is small, the degree of foaming and the viscosity tend to be kept low. Thus, by setting the amount of the dispersant to be used so as to be not less than the lower limit, the raw material mixture can be emulsified uniformly, so that it is possible to limit the particle size distribution in a narrow range and also to inhibit particle agglutination. On the other hand, by setting the amount of the dispersant so as to be not more than the upper limit, it is possible to inhibit the occurrence of foaming and the increase in viscosity, so that the porous particles can be produced easily.

In the polymerization step, the reaction temperature is not particularly limited, and can be set as appropriate. The reaction temperature is determined basically depending on the combination of an epoxy resin and a curing agent, and is, for example, 20° C. to 250° C., 40° C. to 220° C., or 50° C. to 200° C., while it may vary depending on the stirring speed, the amounts of the porogen and the surfactant to be used, etc. The heating temperature affects the pore diameter of porous particles to be obtained, for example. When the heating temperature is high, porous particles to be obtained tend to have a small pore diameter. When the heating temperature is low, porous particles to be obtained tend to have a large pore diameter. When the heating temperature is moderately high, an addition polymerization reaction proceeds smoothly. When the heating temperature is moderately low, the reaction velocity can be prevented from being too high, so that the pore structure can be formed successfully.

In the polymerization step, the reaction time also is not particularly limited, and can be set as appropriate. The reaction time is, for example, 0.01 to 100 hours, 0.05 to 24 hours, or 0.1 to 20 hours, while it may vary depending on the stirring speed, the heating temperature, the amounts of the porogen and the surfactant used, etc. The reaction time affects the reaction rate of porous particles to be obtained, for example. When the reaction time is long, the amount of unreacted substances is small owing to a high reaction rate, so that the porous particles tend to have high mechanical strength. When the reaction time is short, the amount of unreacted substances is large owing to a low reaction rate, so that the porous particles tend to have low mechanical strength. When the reaction time is moderately long, an addition polymerization reaction proceeds sufficiently, thus allowing a desired pore structure to be formed. When the reaction time is moderately short, it is possible to reduce the risk of fracture etc. caused by stirring.

In the polymerization step, it is preferable to perform the reaction while stirring the dispersion. The stirring speed is not particularly limited, and is, for example, 10 to 20,000 rpm, 30 to 10,000 rpm, 50 to 5,000 rpm, 50 to 800 rpm, or 100 to 400 rpm, while it may vary depending on the heating temperature, the reaction scale, the amounts of the porogen and the surfactant to be used, etc. The "rpm" stands for revolutions per minute. The stirring speed affects the particle size of the porous particles to be obtained, for example. In general, when the stirring speed is high, the porous particles to be obtained tend to have a small particle size, and when the stirring speed is low, the porous particles tend to have a large particle size. When the stirring speed is moderately high, the phase separation etc. are inhibited, so that porous particles with a uniform particle size can be obtained. When the stirring speed is moderately low, it is possible to prevent the particle size from being too small and also to inhibit the occurrence of foaming.

After the completion of the polymerization step, the porogen, the solvent, the unreacted substances, and the like are removed from the porous particles (particulate cured products), when necessary, as described above. Specifically, for example, the dispersion medium containing the porous particles is washed sufficiently by repeating an operation of diluting the dispersion medium with a large amount of a washing solvent and separating the settling particles by centrifugation, and thereafter, the washing solvent is removed using a vacuum dryer. The washing solvent preferably is a solvent that is highly soluble in the dispersion medium and the porogen or a solvent that has a low boiling point and thus can be removed easily. Specific examples of the washing solvent include tetrahydrofuran. In this manner, the porous particles of the present invention can be obtained. As described above, the material of the porous particles of the present invention is not particularly limited. For example, in the case of forming porous particles using a material other than thermosetting resins, a porous particle raw material corresponding to the material of the porous particles may be used instead of the porous particle raw material containing a thermosetting monomer and/or a thermosetting prepolymer, and it is not necessary to use a porogen or a curing agent.

The produced porous particles may be subjected to surface modification or the like by a physical or chemical treatment, for example. The physical or chemical treatment may be carried out for the purpose of improving the properties of the porous particles as a separating agent for chromatography, for example. Examples of the physical or chemical treatment include surface hydrophilization, surface hydrophobization, and introduction of a functional group(s).

The use of the porous particles of the present invention is not particularly limited. For example, the porous particles of the present invention are very useful as a novel adsorptive separating agent. More specifically, the porous particles of the present invention can be used as a separating agent for chromatography, for example. Examples of a target substance to be separated by chromatography include: biological substances such as proteins, peptides, amino acids, and nucleic acids; and other chemical substances. The use of the porous particles of the present invention is not limited thereto. For example, the porous particles of the present invention are applicable to various uses, and can be used as, for example, fillers for use in cosmetics, fillers for use tires, fillers for use in paint and ink, excipients for sustained-release drugs, fillers for use in column reactors carrying a reaction catalyst, disinfectants, and battery separators. For example, when the porous particles of the present invention are used as a battery separator, the battery separator can be obtained by coating surfaces of electrodes with the porous particles of the present invention.

EXAMPLES

Examples of the present invention will be described below. It is to be noted, however, that the present invention is by no means limited to the following examples.

Synthesis Examples: Synthesis of A-B Block Copolymer (Dispersant)

In the manners described in the following Synthesis Examples 1 to 2, A-B block copolymers (dispersants) each composed of a hydrophobic polymer block A and a hydrophilic polymer block B were produced (synthesized). Monomers composing these block copolymers were all (meth)acrylate monomers. The A-chain polymer block was composed of (meth)acrylate having a hydrophobic group, and the B-chain polymer block was composed of (meth)acrylate having a hydrophilic group. These block copolymers each had a polystyrene-equivalent number-average molecular weight determined by GPC of 2,000 to 100,000 and had a PDI of 1.6 or less. In each of the block copolymers, the polymer block A composed of the (meth)acrylate having a hydrophobic group had a number average molecular weight of less than 80,000, and the amount of the polymer block A was 20 to 95 mass % of the total amount of all the components. Unless otherwise stated, parts of each substance given below mean parts by mass (parts by weight).

Synthesis Example 1

To a reaction vessel having a stirrer, a reflux condenser, a thermometer, and a nitrogen inlet tube attached thereto, 5.23 parts of toluene, 5 parts of laurylmethacrylate (abbreviated as "LMA" hereinafter), 0.0495 parts of iodine, 0.909 parts of 2,2'-azobis(4-methoxy-2,4-dimethylvaleronitrile) (abbreviated as "V-70" hereinafter) as a polymerization initiator, 0.0183 parts of azobisdimethylvaleronitrile (abbreviated as "V-65" hereinafter), and 0.0726 parts of tetrabutylammonium iodide (abbreviated as "BNI" hereinafter) were added, and the resultant mixture was stirred at 60° C. while supplying nitrogen. Polymerization was allowed to proceed for 16 hours, whereby a polymer block A was obtained. A sample was extracted from the polymer block A, and the solid content in the sample was measured. The polymerization conversion calculated from the nonvolatile content was 90%. The number-average molecular weight (abbreviated as "RI-Mn" hereinafter) measured by a differential refractometer of a GPC apparatus at this time was 16,500, and the PDI was 1.27.

Next, 2.33 parts of toluene, 9.34 parts of polyethylene glycol methacrylate (abbreviated as "PEGMA" hereinafter), and 0.121 parts of V-70 were added, and polymerization was allowed to proceed for 3 hours at the same temperature as in the above (60° C.), whereby a B-chain was formed. The B-chain had a number-average molecular weight of 2,100, a PDI of 1.28, and a polymerization conversion of 87%. In the above-described manner, an A-B block copolymer solution was obtained. This polymerization solution was dissolved in tetrahydrofuran having substantially the same weight as the polymerization solution, and then precipitated with a large amount of methanol. After allowing the resultant mixture to stand still for a while, the supernatant was removed, and the remaining mixture was centrifuged. Thereafter, the obtained precipitate was subjected to the same step as described above (dissolved in tetrahydrofuran and precipitated with methanol) twice, and the obtained precipitate was then dried. As a result, a A-B block copolymer (dispersant) in a semi-liquid state was obtained. The yield was 41%. The thus-obtained A-B block copolymer had a number-average molecular weight of 18,700 and a PDI of 1.27. The block copolymer (dispersant) of the present synthesis example (Synthesis Example 1) obtained in the above-described manner is referred to as "block copolymer K-1" hereinafter.

Synthesis Example 2

To a reactor having a stirrer, a reflux condenser, a thermometer, and a nitrogen inlet tube attached thereto, 33.4 parts of dimethyldiglycol (abbreviated as "DMDG" hereinafter), 100 parts of LMA, 1.5 parts of iodine, 0.7 parts of tetrabutylammonium iodide (abbreviated as "BNI" hereinafter), 3.8 parts of 2,2'-azobis(4-methoxy-2,4-dimethylvaleronitrile) (trade name: V-70, Wako Pure Chemical Industries, Ltd.) as a polymerization initiator, and 1.0 parts of 2,2'-azobis(2,4-dimethylvaleronitrile) (trade name: V-65, Wako Pure Chemical Industries, Ltd.) were added. The resultant mixture was stirred while introducing argon gas and heated to 60° C. using a heating mantle. Polymerization was allowed to proceed for 3 hours while keeping the temperature thereof at 60° C., whereby a polymer block A was obtained. The progress of the polymerization was calculated by $^1$H-NMR measurement of the reaction system. As a result, it was found that the conversion was 89%. Further, the molecular weight was calculated by gel permeation chromatography (GPC) measurement (detector: differential refractometer) using a THF solvent. As a result, it was found that the number-average molecular weight (abbreviated as "Mn" hereinafter) was 5900 and the weight-average molecular weight (abbreviated as "Mw" hereinafter) was 8200. The molecular weight distribution (abbreviated as "PDI value" hereinafter) thereof was 1.40.

Subsequent to the above process, 147 parts of PEGMA, 0.7 parts of V-65, and 49 parts of DMDG were added to the reaction system. Polymerization was allowed to proceed at 60° C. for a predetermined time (1 hour), whereby a polymer block B was formed. The progress of the polymerization was calculated by $^1$H-NMR measurement. As a result, it was found that the conversion of the PEGMA was 23%. Further, the molecular weight was measured by GPC. As a result, it was found that the block copolymer as a whole had Mn of 9700 and Mw of 12000. The PDI value was 1.24.

337 parts of the polymerization solution obtained in the above-described manner was diluted with substantially the same amount of THF and then washed with saturated saline to remove DMDG and unreacted PEGMA. The remaining mixture was dried over sodium sulfate, concentrated, and dried at 80° C. As a result, 118 parts of a high molecular weight additive composed of an A-B block copolymer was obtained. In the case where the DMDG and the unreacted PEGMA could not be removed completely by the washing operation, the mixture was subjected to dialysis (dialysis membrane: Spectra/Por 6, MWCO 1,000) in water, and then freeze-dried. The block copolymer (dispersant) of the present synthesis example (Synthesis Example 2) obtained in the manner described above is referred to as "block copolymer K-2" hereinafter.

The porous particles of the present invention were produced in the following respective examples.

Example 1

(Preparation of Epoxy Monomer Composition)

As an epoxy monomer, 2.00 parts by weight of an epoxy compound (trade name "TETRAD-C", Mitsubishi Gas Chemical Company, Inc) represented by the following formula (1) and having an epoxy equivalent of 95 to 110 (102 on average) was used. As a curing agent, 1.15 parts by weight of bis(4-aminocyclohexyl)methane (Tokyo Chemical Industry Co., Ltd.) represented by the following formula (2) and having an amine value of 520 to 550 was used. As a porogen, 8 parts by weight of polyethylene glycol 200 (Wako Pure Chemical Industries, Ltd.) represented by the following formula (3) and having an average molecular weight of 200 was used. They were mixed together for 5 minutes using a planetary centrifugal mixer "Awatori Rentaro" (trade name, THINKY CORPORATION). Thus, an epoxy monomer composition was obtained.

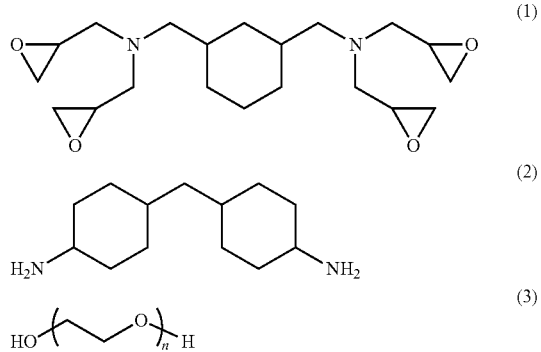

(Dispersion Preparation Step)

In a cylindrical glass sample bottle (inner diameter: 19 mm, height: 60 mm), 11.15 g of the epoxy monomer composition obtained in the above was added to a mixture obtained by dissolving 0.6 g of the above block copolymer (dispersant) K-1 in 10 g of dodecane as a dispersion medium. Thus, a dispersion was prepared.

(Polymerization Step and After-Treatment)

The dispersion was stirred with stirring blades rotated at 2000 rpm for 30 minutes at an ordinary temperature to achieve emulsified dispersion. Thereafter, the number of revolutions per minute was reduced to 50 rpm, which is the number of revolutions per minute sufficient to prevent the particles from settling down or binding to each other, and the dispersion was stirred in a high temperature bath at 140° C. for 60 minutes to cause polymerization. The product obtained through the polymerization was added to MEK, and the resultant mixture was stirred sufficiently.

Figure 2:
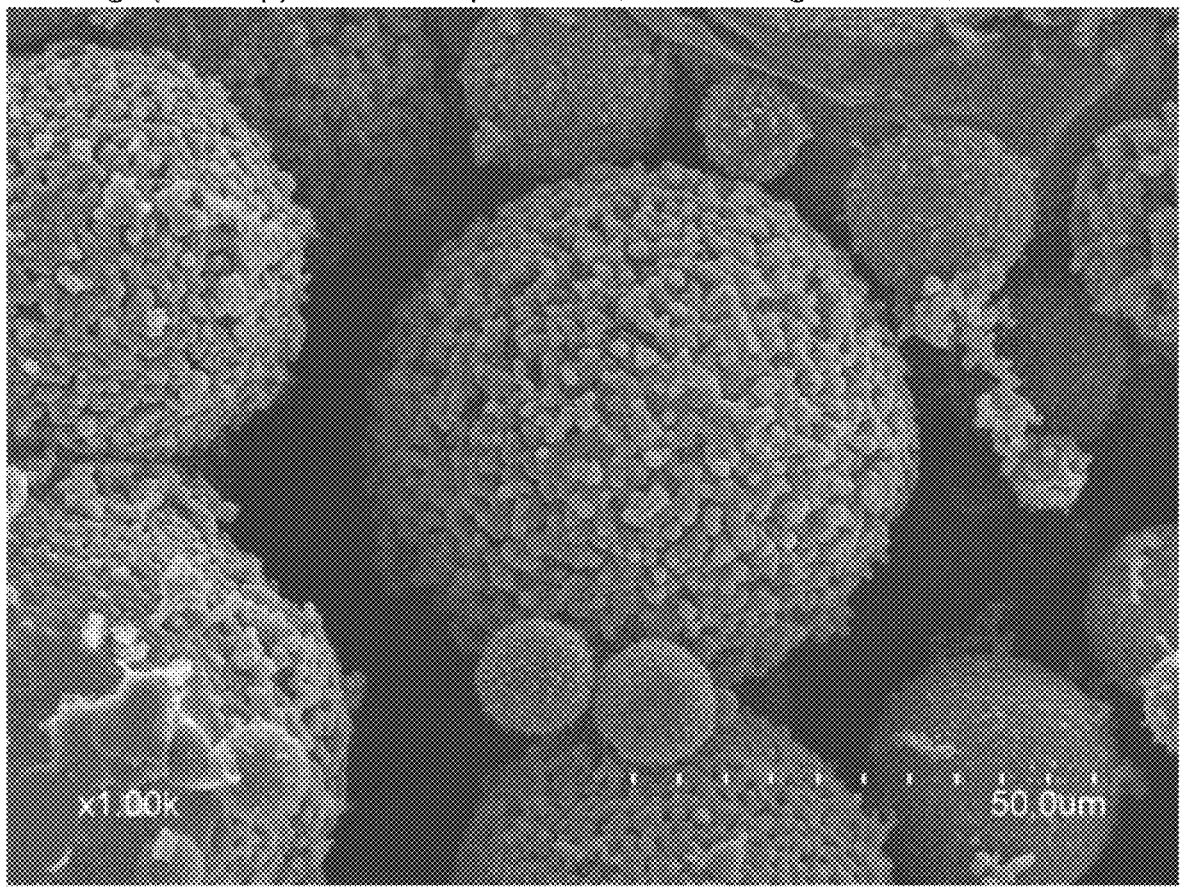
FIG. 2 is a photograph showing the appearance of the epoxy resin porous particles produced in the example (1000× magnification).
Figure 3:
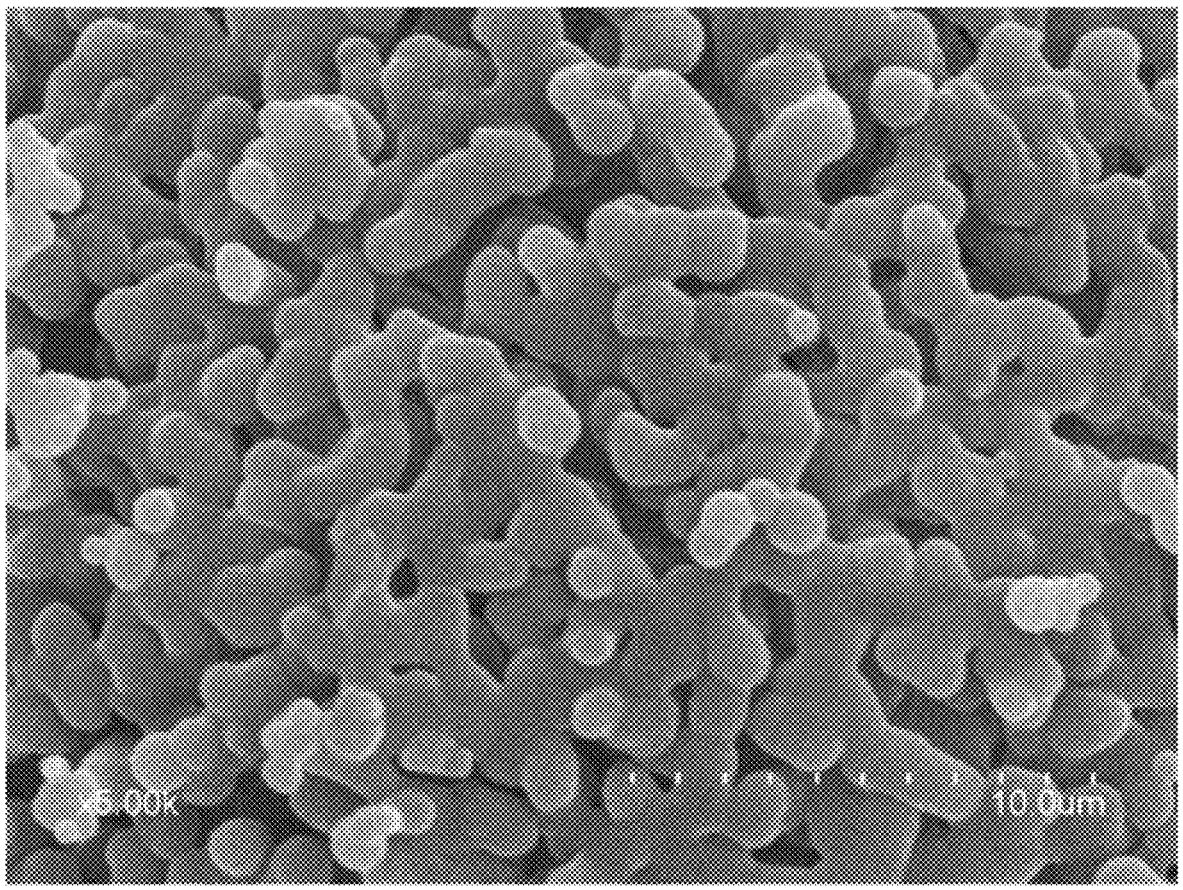
FIG. 3 is a photograph showing the appearance of the epoxy resin porous particles produced in the example (5000× magnification).
Figure 4:
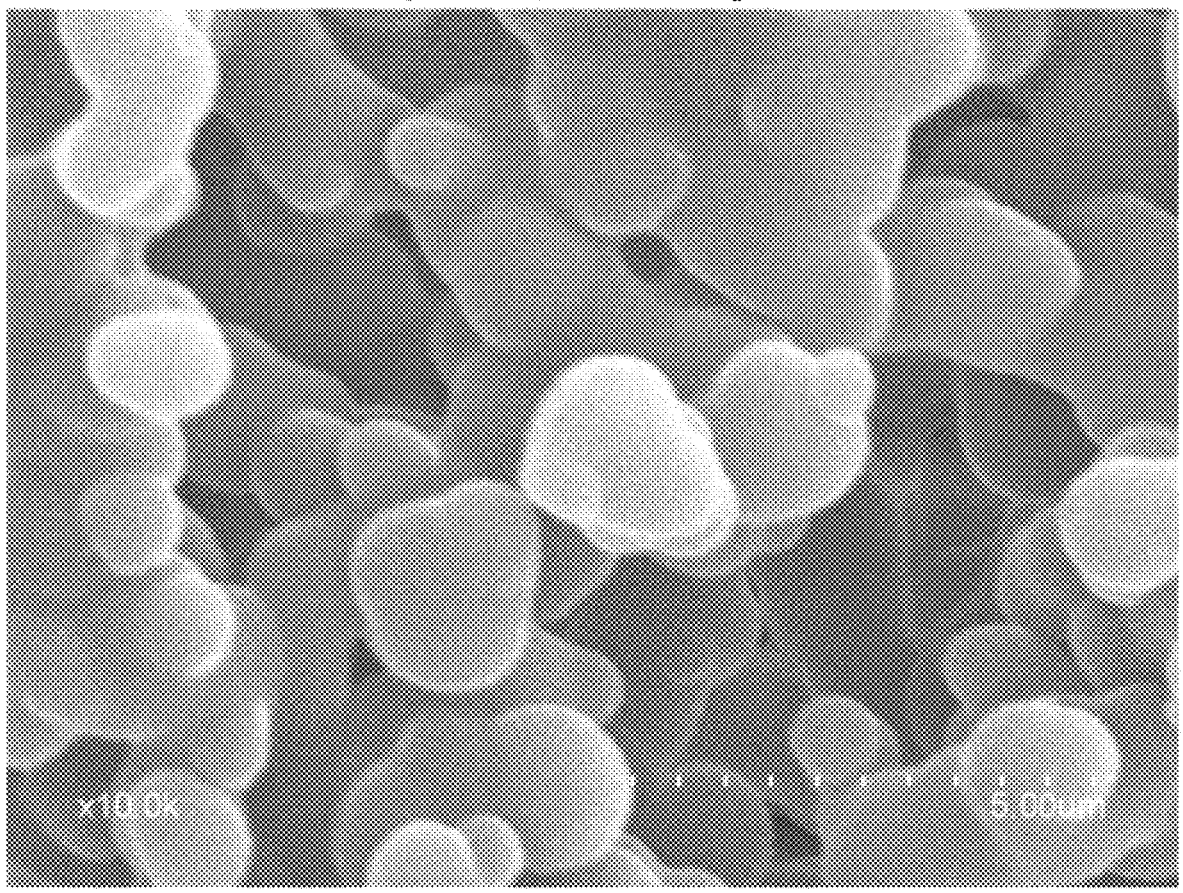
FIG. 4 is a macrophotograph showing the cross section of the epoxy resin porous particles produced in the example (10000× magnification).

Thereafter, the mixture was centrifuged to separate particles. This washing step using the MEK was repeated to a total of 10 times to remove the porogen, the remaining monomer, and the like sufficiently. Thereafter, the remaining mixture was vacuum-dried. As a result, 2.85 g of spherical epoxy resin porous particles were obtained. The mean particle size of the porous particles was 28 μm. SEM images showing the appearance of the spherical porous particles (spherical fine particles) and the surface and the inside of the particle are shown in FIGS. 1 to 4. FIG. 1 is a photograph showing the appearance of the epoxy resin porous particles produced in Example 1 (250× magnification). FIG. 2 is a photograph showing the appearance of the epoxy resin porous particles produced in Example 1 (1000× magnification). FIG. 3 is a photograph showing the appearance of the epoxy resin porous particles produced in Example 1 (5000× magnification). FIG. 4 is a macrophotograph showing the cross section of the epoxy resin porous particle produced in Example 1 (10000× magnification). As can be seen from FIGS. 1 to 4, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 2

2.75 g of spherical epoxy resin porous particles were obtained in the same manner as in Example 1, except that the reaction temperature in the polymerization step was set to 150° C. The mean particle size of the porous particles was 30 μm. SEM images showing the appearance of the spherical porous particles (spherical fine particles) and the surface and the inside of the particle exhibited results similar to those shown in FIGS. 1 to 4 (Example 1). That is, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 3

2.5 g of spherical epoxy resin porous particles were obtained in the same manner as in Example 1, except that, as the dispersant, the block copolymer K-2 was used instead of the block copolymer K-1. The mean particle size of the porous particles was 33 μm. SEM images showing the appearance of the spherical porous particles (spherical fine particles) and the surface and the inside of the particle exhibited results similar to those shown in FIGS. 1 to 4 (Example 1). That is, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 4

(Preparation of Epoxy Monomer Composition)

As an epoxy monomer, 1.6 parts by weight of an epoxy compound "isocyanuric acid triglycidyl" (trade name "TEPIC-S", NISSAN CHEMICAL INDUSTRIES, LTD.) represented by the following formula (4) and having an epoxy equivalent of 99 was used. As a curing agent, 0.37 parts by weight of bis(4-aminocyclohexyl)methane (Tokyo Chemical Industry Co., Ltd.) represented by the above formula (2) and having an amine value of 520 to 550 was used. As a porogen, 7 parts by weight of polyethylene glycol 200 (Wako Pure Chemical Industries, Ltd.) represented by the above formula (3) and having an average molecular weight of 200 was used. The "TEPIC-S" and the PEG 200 were melted by heating at 110° C. Also, the curing agent was melted by heating at 85° C. separately. They were mixed together in a vortex mixer rotated at 3000 rpm for a few minutes. Thus, an epoxy monomer composition was obtained.

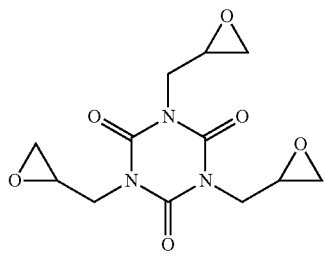

(4)

(Dispersion Preparation Step)

In a cylindrical glass sample bottle (inner diameter: 19 mm, height: 60 mm), 8.97 g of the epoxy monomer composition obtained in the above was added to a mixture obtained by dissolving 0.6 g of the above block copolymer (dispersant) K-1 in 10 g of dodecane as a dispersion medium. The resultant mixture was stirred using a vortex mixer until the emulsified state became seemingly stable (6 to 10 minutes). Thus, a dispersion was prepared. Prior to the preparation of the dispersion, the dispersion medium was preheated to 50° C. or higher.

(Polymerization Step and After-Treatment)

The dispersion was stirred with stirring blades rotated at 50 rpm in a high temperature bath at 90° C. for 180 minutes to cause polymerization. The product obtained through the polymerization was added to tetrahydrofuran, and the resultant mixture was stirred sufficiently. Thereafter, the mixture was centrifuged to separate particles. This washing step using the tetrahydrofuran was repeated to a total of 10 times to remove the porogen, the remaining monomer, and the like sufficiently. Thereafter, the remaining mixture was vacuum-dried. As a result, 1.75 g of spherical epoxy resin porous particles were obtained. The mean particle size of the porous particles was 29 μm. SEM images showing the appearance of the spherical porous particles (spherical fine particles) and the surface and the inside of the particle exhibited results similar to those shown in FIGS. 1 to 4 (Example 1). That is, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 5

Porous particles were produced under the same conditions as in Example 4, except that the polymerization temperature was set to 80° C. As a result, 1.83 g of spherical porous particles were obtained. The mean particle size of the porous particles was 26 μm. SEM images showing the appearance of the spherical porous particles (spherical fine particles) and the surface and the inside of the particle exhibited results similar to those shown in FIGS. 1 to 4 (Example 1). That is, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 6

Porous particles were produced under the same conditions as in Example 4, except that the polymerization was caused using 8.4 parts of PEG 200, 0.67 parts of the dispersant, and 9 parts of the dispersion medium. As a result, 1.85 g of spherical porous particles were obtained. The mean particle size of the porous particles was 38 μm. SEM images showing the appearance of the spherical porous particles (spherical fine particles) and the surface and the inside of the particle exhibited results similar to those shown in FIGS. 1 to 4 (Example 1). That is, these epoxy resin porous particles each had an interconnected pore structure in which through holes provided inside the porous particle communicate with each other. Further, these epoxy resin porous particles had no skin layer on their surfaces, and ends of the through holes were open toward the outside of the porous particles.

Example 7

(Preparation of Acrylic Monomer Composition)

A solution was obtained by uniformly dissolving 0.41 g of polyethylene oxide (Aldrich, the average molecular weight: 100,000) as a phase separation inducing component in 10 g of dimethylformamide (Nacalai Tesque, Inc.) as a solvent in a screw cap bottle at 60° C. After cooling the solution to room temperature, 3.35 g of glycerol dimethacrylate (GDMA, Kyoeisha Chemical Co., Ltd., GP-101P, molecular weight: 227) was added to the solution as a monomer, and the resultant mixture was stirred to prepare a uniform solution. Further, as an initiator and reversible transfer catalysts, 0.04 g of 2,2'-azobis(2,4-dimethylvaleronitrile) (Wako Pure Chemical Industries, Ltd.), 0.02 g of iodine (Tokyo Chemical Industry Co., Ltd.), and 0.002 g of N-iodosuccinimide (Tokyo Chemical Industry Co., Ltd.) were added to the solution, and the resultant mixture was stirred to prepare a uniform solution. Next, bubbles in this polymerization solution were removed using an ultrasonic device. Thereafter, nitrogen gas bubbling was performed to replace remaining oxygen with nitrogen.

(Dispersion Preparation Step)

In a cylindrical glass sample bottle (inner diameter: 19 mm, height: 60 mm), 13.80 g of the acrylic monomer composition obtained in the above was added to a mixture obtained by dissolving 0.30 g of the above block copolymer (dispersant) K-1 in 5 g of dodecane as a dispersion medium. The resultant mixture was stirred using a vortex mixer rotated at 3000 rpm until the emulsified state became seemingly stable (6 to 10 minutes). Thus, a dispersion was prepared.

(Polymerization Step and After-Treatment)

Figure 5:
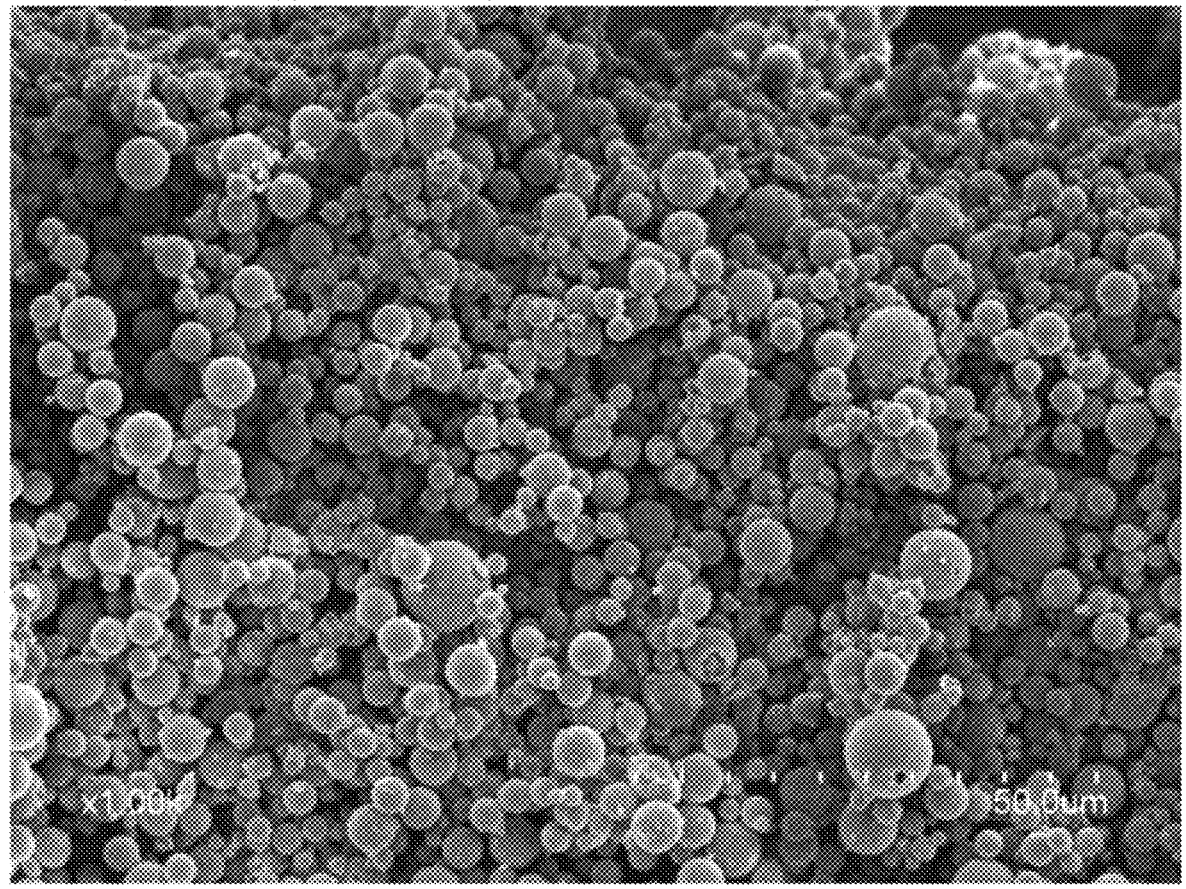
FIG. 5 is a photograph showing the appearance of acrylic porous particles produced in another example (1000× magnification).
Figure 6:
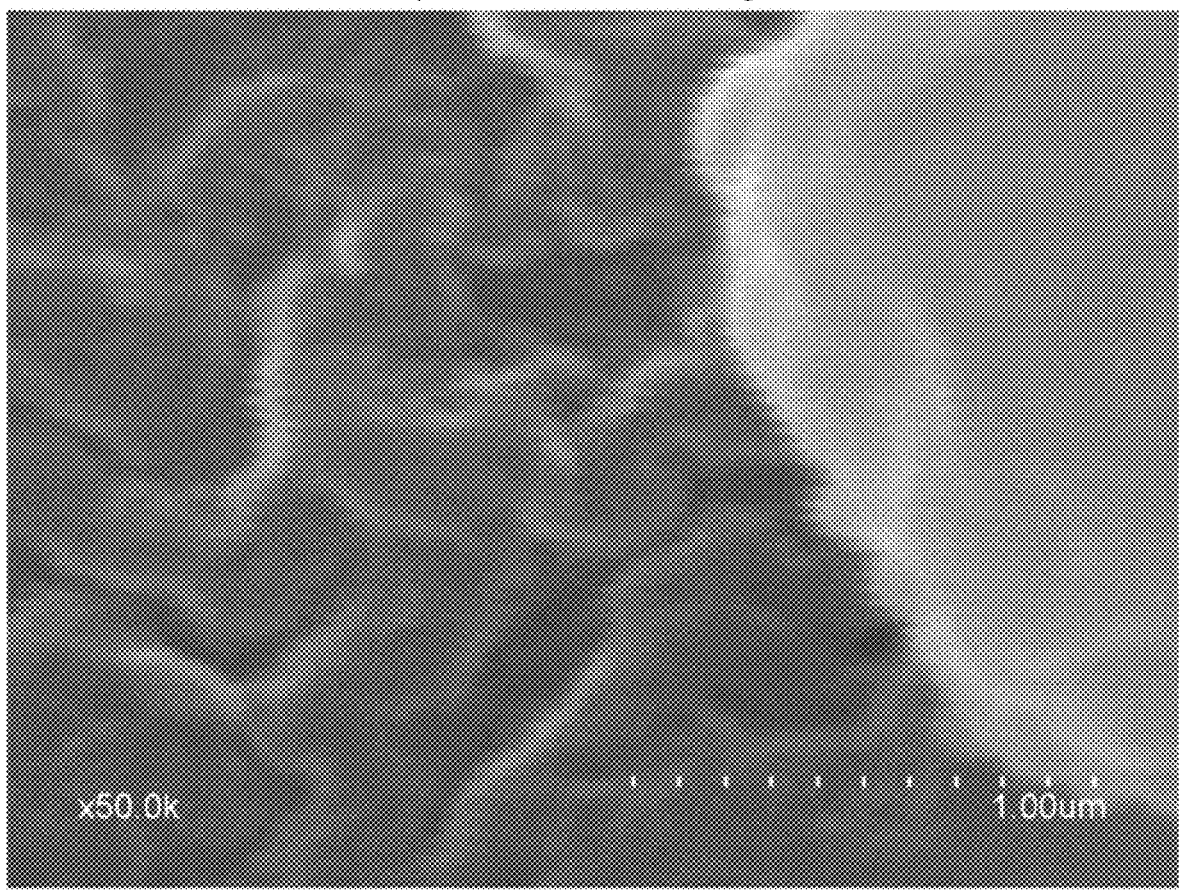
FIG. 6 is a photograph showing the internal cross section of the acrylic porous particles produced in the example (50000× magnification).

The dispersion was stirred with stirring blades rotated at 50 rpm in a high temperature bath at 100° C. for 8 hours to cause a polymerization reaction. Thereafter, the obtained high molecular weight polymer was cooled to room temperature, and then taken out from the container. The high molecular weight polymer was washed with acetone and methanol, and then vacuum-dried. As a result, 2.1 g of spherical acrylic resin porous particles were obtained. The mean particle size of the porous particles was 25 μm. The appearance and the internal cross-sectional structure of this porous material were examined under a scanning electron microscope. As a result, it was found that the porous material had formed a co-continuous structure having pores with a pore size of about 0.1 μm, as shown in FIGS. 5 and 6.

Data obtained in Examples 1 to 7 are shown in Tables 1 to 3 below.

TABLE 1

|  | Name of raw material or unit | Ex. 1 | Ex. 2 | Ex. 3 |
|---|---|---|---|---|
| Epoxy monomer | TETRAD-C | 2 | 2 | 2 |
|  | TEPIC-S |  |  |  |
| Curing agent | bis(4-aminocyclohexyl)methane | 1.15 | 1.15 | 1.15 |
| Porogen | polyethylene glycol 200 | 8 | 8 | 8 |
| Subtotal |  | 11.15 | 11.15 | 11.15 |
| Dispersant | K-1 | 0.6 | 0.6 |  |
|  | K-2 |  |  | 0.6 |
| Dispersion medium | dodecane | 10 | 11 | 12 |
| Total |  | 21.75 | 22.75 | 23.75 |
| Polymerization temperature | ° C. | 140 | 150 | 140 |
| Polymerization time | min | 60 | 60 | 60 |
| Yield | g | 2.85 | 2.75 | 2.5 |
| Mean particle size | μm | 28 | 30 | 33 |
| Pore diameter | nm | 950 | 750 | 900 |

TABLE 2

|  | Name of raw material or unit | Ex. 4 | Ex. 5 | Ex. 6 |
|---|---|---|---|---|
| Epoxy monomer | TETRAD-C |  |  |  |
|  | TEPIC-S | 1.6 | 1.6 | 1.6 |
| Curing agent | bis(4-aminocyclohexyl)-methane | 0.37 | 0.37 | 0.37 |
| Porogen | polyethylene glycol 200 | 7 | 7 | 8.4 |
| Subtotal |  | 8.97 | 8.97 | 10.37 |
| Dispersant | K-1 | 0.6 | 0.6 | 0.67 |
|  | K-2 |  |  |  |
| Dispersion medium | dodecane | 10 | 10 | 9 |
| Total |  | 19.57 | 19.57 | 20.04 |
| Polymerization temperature | ° C. | 90 | 80 | 90 |
| Polymerization time | min | 180 | 180 | 180 |
| Yield | g | 1.75 | 1.83 | 1.85 |
| Mean particle size | μm | 29 | 26 | 38 |

TABLE 3

|  | Name of raw material or unit | Ex. 7 |
|---|---|---|
| Acrylic monomer | glycerol dimethacrylate | 3.35 |
| Phase separation | polyethylene oxide | 0.41 |

TABLE 3-continued

|  | Name of raw material or unit | Ex. 7 |
|---|---|---|
| inducing component |  |  |
| Solvent | dimethylformamide | 10 |
| Subtotal |  | 13.76 |
| Dispersant | K-1 | 0.3 |
|  | K-2 |  |
| Dispersion medium | dodecane | 5 |
| Total |  | 19.06 |
| Polymerization temperature | ° C. | 100 |
| Polymerization time | min | 480 |
| Yield | g | 2.1 |
| Mean particle size | μm | 25 |
| Pore diameter | nm | 100 |

Further, the porous particles of Examples 1 to 7 were used as separating agents for chromatography. As a result, they all exhibited favorable separation properties.

INDUSTRIAL APPLICABILITY

As specifically described above, the present invention can provide porous particles made of an organic polymer, uniform in shape, and having through holes that are not closed, a method for producing the particles, and a block copolymer for use in the production method. The use of the porous particles of the present invention is not particularly limited. For example, the porous particles of the present invention are very useful as a novel adsorptive separating agent. More specifically, the porous particles of the present invention can be used as a separating agent for chromatography, for example. Examples of a target substance to be separated by chromatography include: biological substances such as proteins, peptides, amino acids, and nucleic acids; and other chemical substances. The use of the porous particles of the present invention is not limited thereto. For example, the porous particles of the present invention are applicable to various uses, and can be used as, for example, fillers for use in cosmetics, fillers for use tires, fillers for use in paint and ink, excipients for sustained-release drugs, and fillers for use in column reactors carrying a reaction catalyst.

The invention claimed is:

1. Porous particles having a substantially spherical shape, wherein
    the porous particles are made of an organic polymer,
    each of the porous particles has an interconnected pore structure in which through holes provided inside the porous particle communicate with each other,
    the through holes have a co-continuous structure,
    the through holes are formed by spinodal decomposition, and
    ends of the through holes are open toward an outside of the porous particle.

2. The porous particles according to claim 1, wherein each of the porous particle is shaped so that the longest diameter is not more than 1.6 times the shortest diameter.

3. The porous particles according to claim 1, having a mean particle size in a range from 0.5 to 30,000 μm.

4. A method for producing the porous particles according to claim 1, the method comprising:
    a dispersion preparation step of preparing a dispersion by dispersing a porous particle raw material comprising an organic monomer and/or an organic prepolymer in a dispersion medium; and a polymerization step of polymerizing the porous particle raw material in the dispersion, wherein, in the polymerization step, the through holes are formed by spinodal decomposition.

5. The method according to claim 4, wherein in the dispersion preparation step, the porous particle raw material is dispersed in the dispersion medium together with a dispersant.

6. The method according to claim 5, wherein the dispersant is a block copolymer comprising a hydrophobic polymer block and a hydrophilic polymer block.

7. The method according to claim 6, further comprising a dispersant production step of producing the dispersant, the dispersant production step comprising:

a first living radical polymerization step of forming one of the hydrophobic polymer block and the hydrophilic polymer block by living radical polymerization; and a second living radical polymerization step of forming the other one of the hydrophobic polymer block and the hydrophilic polymer block by living radical polymerization after the first living radical polymerization step.

8. The method according to claim 5, wherein the dispersant is a surfactant.

9. A block copolymer comprising:

a hydrophobic polymer block; and a hydrophilic polymer block, wherein the block copolymer is used as the dispersant in the method according to claim 6.

* * * * *